(12) United States Patent
Anderson

(10) Patent No.: US 10,667,807 B2
(45) Date of Patent: Jun. 2, 2020

(54) APPARATUS AND METHOD FOR TISSUE ADHESION

(71) Applicant: MICROKOLL, INC., Lompoc, CA (US)

(72) Inventor: Steven Craig Anderson, Lompoc, CA (US)

(73) Assignee: MICOKOLL INC., Lompoc, CA (US)

( * ) Notice: Subject to any disclaimer, the term of this patent is extended or adjusted under 35 U.S.C. 154(b) by 434 days.

(21) Appl. No.: 15/601,187

(22) Filed: May 22, 2017

(65) Prior Publication Data

US 2017/0303917 A1 Oct. 26, 2017

Related U.S. Application Data

(63) Continuation of application No. 13/583,199, filed as application No. PCT/US2011/028022 on Mar. 11, 2011, now Pat. No. 9,687,229.

(Continued)

(51) Int. Cl.
*A61B 17/064* (2006.01)
*A61B 17/00* (2006.01)

(52) U.S. Cl.
CPC ........ *A61B 17/064* (2013.01); *A61B 17/0644* (2013.01); *A61B 2017/00526* (2013.01);
(Continued)

(58) Field of Classification Search
CPC ... A61B 17/064; A61B 17/0644; A61B 17/68; A61B 17/846; A61B 17/0641; A61B 17/0642; A61B 17/0643; A61B 2017/00526; A61B 2017/00867; A61B 2017/00871; A61B 2017/0641; A61B 2017/0647; A61B 2017/0645; A61B 2017/0649; A61L 2400/16; C08L 2201/12;
(Continued)

(56) References Cited

U.S. PATENT DOCUMENTS 5,324,307 A * 6/1994 Jarrett .................. A61B 17/064
606/219
8,808,294 B2 * 8/2014 Fox .................... A61B 17/0642
606/75

(Continued)

*Primary Examiner* — Adam J Eiseman
*Assistant Examiner* — Mohammed S. Alawadi
(74) *Attorney, Agent, or Firm* — Felix L. Fischer

(57) ABSTRACT

Shape memory tissue engagement elements (15) are created using shape memory alloys or shape memory (SM) composite sheets (33, 36) with one or more SM material sheets (20, 32). Arrays of the tissue engagement elements may then be inserted or molded into flexible base materials forming pads for tissue engagement. In certain embodiments, the composite sheets incorporate two SM material layers (20, 32) having differing transition temperatures to allow activation of one layer for tissue engagement and activation of the second layer for tissue release. In exemplary embodiments, insertion of interconnected tissue engagement elements (46) into a base layer (19) with slots (48) provides a completed pad array. In alternative exemplary embodiments, vacuum forming of composite sheets (51) with cutting of corrugated sides (53) to form tissue engagement elements allow production of complete arrays of tissue engagement elements. Overmolding the arrays with a flexible base material (19) provides a completed pad.

8 Claims, 25 Drawing Sheets

Related U.S. Application Data

(60) Provisional application No. 61/313,036, filed on Mar. 11, 2010.

(52) U.S. Cl.
CPC .............. *A61B 2017/00867* (2013.01); *A61B 2017/00871* (2013.01); *A61B 2017/0641* (2013.01); *A61B 2017/0647* (2013.01); *A61L 2400/16* (2013.01); *C08L 2201/12* (2013.01)

(58) Field of Classification Search
CPC ...... A61F 2/88; B21F 3/00; B21F 3/04; B21F 45/008; B21F 45/24
USPC ...................................... 72/324; 606/219, 75
See application file for complete search history.

(56) References Cited

U.S. PATENT DOCUMENTS

| | | | |
|---|---|---|---|
| 9,259,222 B2* | 2/2016 | Surti | A61B 17/064 |
| 2004/0073256 A1* | 4/2004 | Marchitto | A61B 17/0487 |
| | | | 606/219 |
| 2006/0100649 A1* | 5/2006 | Hart | A61B 17/0643 |
| | | | 606/157 |
| 2008/0161808 A1* | 7/2008 | Fox | A61B 17/0642 |
| | | | 606/75 |
| 2010/0063506 A1* | 3/2010 | Fox | A61B 17/0642 |
| | | | 606/75 |

\* cited by examiner

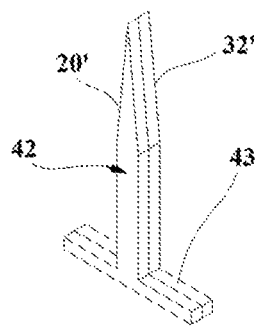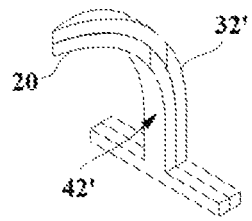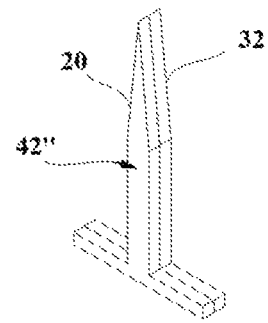
FIGURE 10A  FIGURE 10B  FIGURE 10C
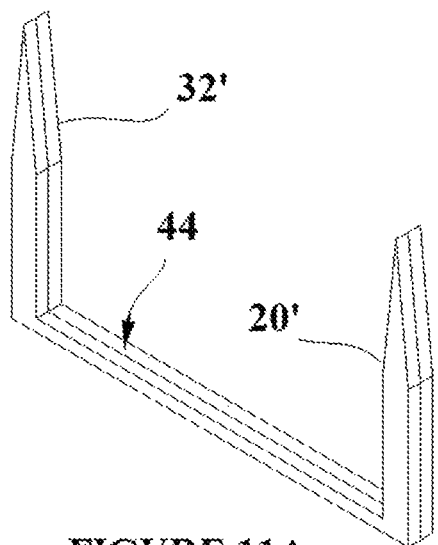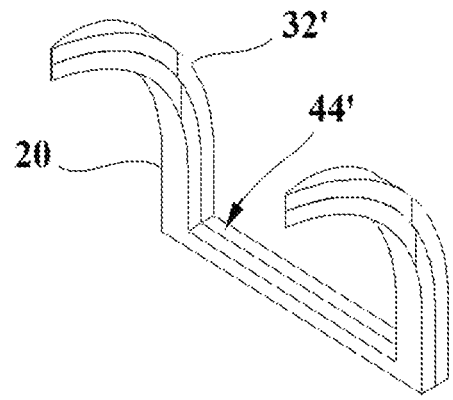
FIGURE 11A  FIGURE 11B
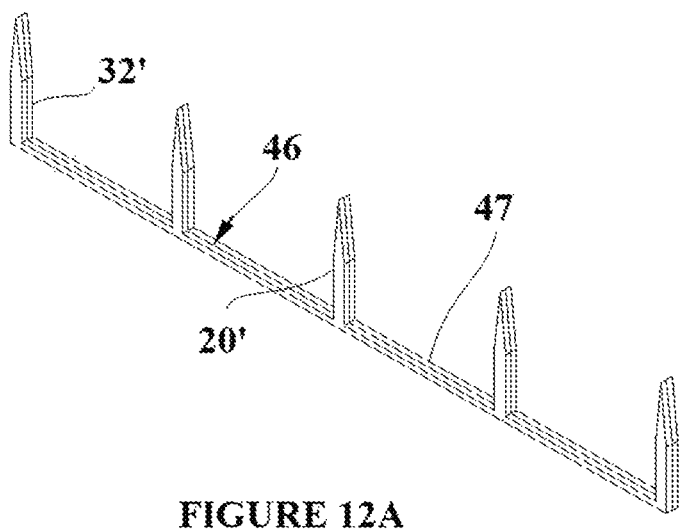
FIGURE 12A

APPARATUS AND METHOD FOR TISSUE ADHESION

REFERENCE TO RELATED APPLICATIONS

This application is a continuation of application Ser. No. 13/583,199 filed on Sep. 6, 2012 which is a 35 U.S.C. 371 filing of international application serial no. PCT/US2011/028022 having an international filing date of Mar. 11, 2011 which claims the priority of U.S. Provisional Application Ser. No. 61/313,036 filed on Mar. 11, 2010 by Steven Craig Anderson entitled Apparatus and Method for Tissue Adhesion, the disclosure of which is incorporated herein by reference.

BACKGROUND

Field

This application relates generally to the field of tissue modification and wound closure and more particularly to potential configurations, manufacturing methods, shape memory activation methods, and treatment applications for tissue capture elements and flexible substrate material embodiments for a substrate supporting a plurality of substantially parallel shape memory microposts for insertion into tissue adjacent a wound or tissue modification site with activation of the shape memory properties of the microposts to deform for adherence to the tissue.

Related Art

Tissue adhesion devices and methods have a wide variety of useful indications. For example, there is currently a need for surface adhesion to tissue for applications such as wound closure and anastomosis, which is the connection of two biological structures such as a vein graft to a coronary artery or the like. Current technologies to address such indications include the use of sutures, staples, or biological adhesives that may be used to join the two sections of tissue together. Each of these technologies has notable limitations. For example, a suture may be deployed into an incision, but tying and placing a proper knot in the suture may require a high degree of experience and manual dexterity and may be difficult for some operators. If the suture knot is not properly tightened, the incision may bleed or be otherwise compromised.

Some surgical staple embodiments may be deployed and secured by a variety of devices and mechanisms, such as by remote mechanical means, into an incision. Staples, however, may not always completely close the wound and may not be re-adjusted, if such adjustment is required, after deployment. In addition, staples tend to be deployed in discrete locations due to their bulk and may produce concentrated stress and strain points within tissue adjacent the deployed staples. Biological adhesives may be applied into a wound, but the presence of blood will often hinder an effectiveness of the adhesion strength between the adhesive and tissue. Also, biological tissue adhesives often tend to be rigid after they have cured, so as to cause stiffness at the point of contact and reduce flexibility of the wound when stress is applied thereto. Such a relatively stiff joint may even fracture or crack when stressed causing the wound to reopen and hemorrhaging to occur.

Copending PCT application serial no. PCT/US09/57348 entitled APPARATUS AND METHOD FOR TISSUE ADHESION and having a common inventor with the present application, the disclosure of which is fully incorporated herein by reference, describes a substrate supporting a plurality of substantially parallel shape memory microposts for insertion into tissue adjacent a wound or tissue modification site with activation of the shape memory properties of the microposts to deform for adherence to the tissue It is therefore desirable to provide configurations, manufacturing methods, shape memory activation methods, and treatment applications for the tissue capture elements and flexible substrate material embodiments for the substrate and the supported substantially parallel shape memory microposts.

SUMMARY

The embodiments disclosed herein provide methods wherein shape memory tissue engagement elements are created using shape memory alloys or shape memory (SM) composite sheets with one or more SM material sheets. Arrays of the tissue engagement elements may then be inserted or molded into flexible base materials forming pads for tissue engagement. In certain embodiments, the composite sheets incorporate two SM material layers having differing transition temperatures to allow activation of one layer for tissue engagement and activation of the second layer for tissue release. In exemplary embodiments, insertion of interconnected tissue engagement elements into a slotted base layer provides a completed pad array. In alternative exemplary embodiments, vacuum forming of composite sheets with cutting of corrugated sides to form tissue engagement elements allow production of complete arrays of tissue engagement elements. Overmolding the arrays with a flexible base material provides a completed pad.

Embodiments employing joined flexible base material having tissue engagement elements extending from both sides of the resulting pad allow for certain wound closure methods. Similarly, folding of pads having tissue engagement members engaged in a tissue layer with adhesive bonding of the folded pad provides an alternative method for wound closure.

Embodiments employing a perforated or porous base layer allow drainage of a closed wound and a compressible foam pad overlaying the shape memory engagement elements insulates from premature activation.

Embodiments employing tissue capture elements having length, l, with shape memory properties activated by temperature allows application of electromagnetic energy to the tissue capture elements having a frequency, f, tuned to the length for activation of the tissue capture elements.

The features, functions, and advantages that have been discussed can be achieved independently in various embodiments of the present invention or may be combined in yet other embodiments further details of which can be seen with reference to the following description and drawings.

BRIEF DESCRIPTION OF THE DRAWINGS

FIGS. 10A-C show of a shape memory polymer tissue capture element created from a dual shape memory polymer sheet;

FIGS. 11A and B show a double shape memory polymer tissue capture element created from a dual shape memory polymer sheet;

DETAILED DESCRIPTION

Figure 1A:
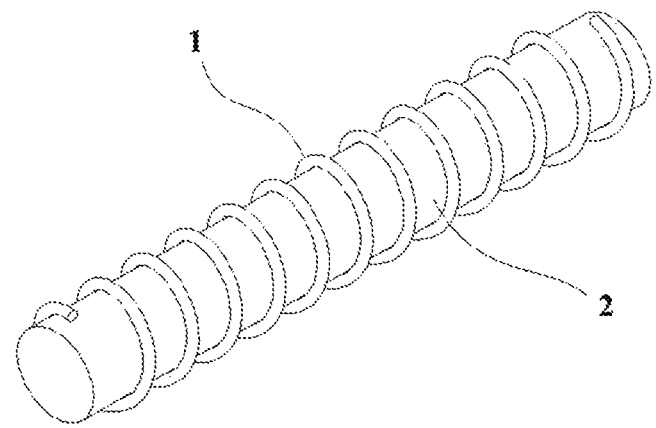
FIGS. 1A-C depict a method for simultaneously setting a permanent shape into multiple shape memory alloy elements using a suitably shaped mandrel.
Figure 1B:
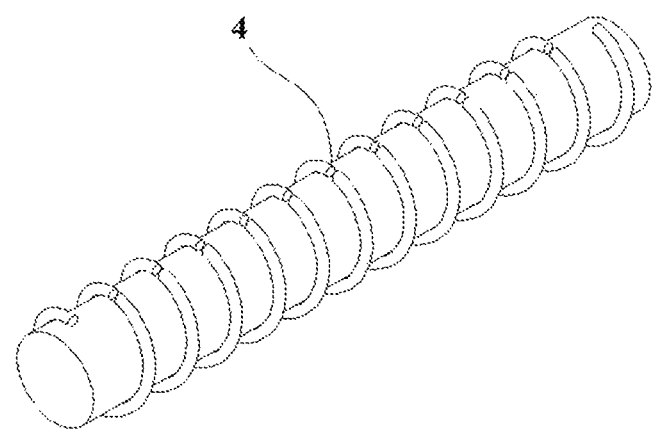
Figure 1C:
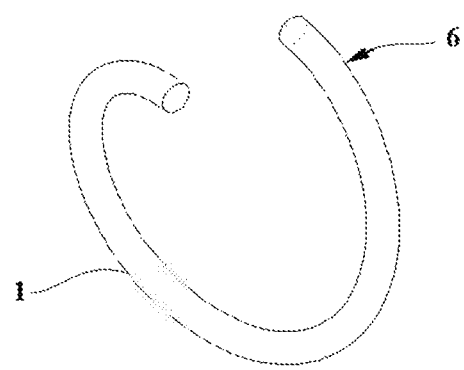

A "permanent" shape can be set into a shape memory alloy (SMA) material by constraining it into the desired shape and then heating it to a specific temperature for a specific period of time. This process is known as shape setting. After the shape setting process, if the SMA material is below its transition temperature (martensite phase), it is malleable and will retain any shape mechanically imparted to it. When the SMA is heated above its transition temperature, it will revert to its permanent shape (austenite phase). FIG. 1A shows shape memory alloy material 1 coiled around a mandrel 2. The SMA material can then be shape set such that the permanent shape of the SMA material 1 is that of the outer surface of the mandrel 2. The coiled SMA material is then cut along a cut line 4 as shown in FIG. 1B. The SMA material could be cut using a laser, e-beam energy, or mechanical methods. FIG. 1C shows an individual element of SMA material 1 in its permanent shape 6. The resulting permanent shape 6 of the SMA material 1 is seen to be the shape of the outer surface of the mandrel 2.

Figure 2A:
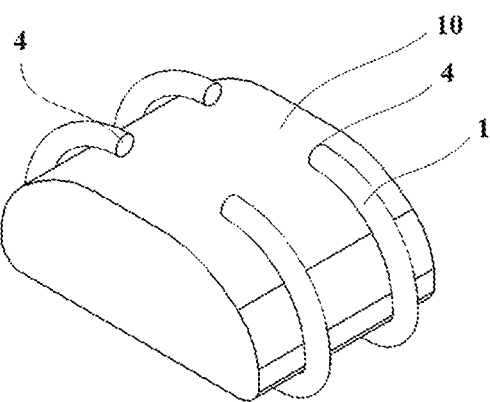
FIGS. 2A-E depict the formation and subsequent processing of a shape memory alloy tissue capture element.
Figure 2B:
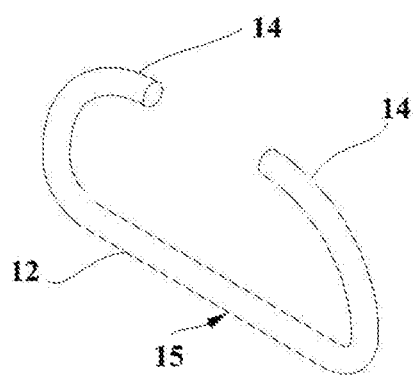
Figure 2C:
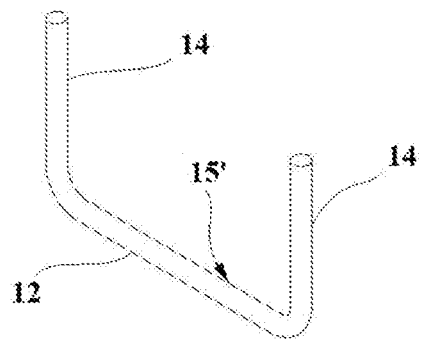

FIGS. 2A-E depict the formation and subsequent processing of a SMA tissue capture element using the method described in the previous paragraph. FIG. 2A shows SMA material 1 coiled around a mandrel 10 with a "D" shaped cross section. Although a "D" shape is depicted in the figure, a mandrel with any suitable cross sectional shape could be used in order to shape set the element. In the figure, the cuts along the cut lines 4 at the crown (greatest radius from the flat base of the mandrel and coil) of the coiled SMA material 1 have already occurred. FIG. 2B shows an individual tissue capture element that has been removed from the mandrel after being cut. The SMA material 1 is shown in its temporary engagement state 15, wherein the arms 14 of the element are curved in towards the base 12 of the element in a configuration suitable for the capture and retention of tissue. FIG. 2C shows the SMA material 1 in a suitable permanent deployment state 15', wherein the arms 14 of the element have been mechanically straightened while the SMA material was at a temperature below its transition temperature. In the deployment state of the element 15', the arms 14 are configured such that they are substantially perpendicular to the base 12 so that they can be more easily deployed into tissue.

The transition of the element between the temporary deployment state 15' and the permanent engagement state 15 allows the element to capture tissue once it has been deployed into that tissue. The element is inserted into the target tissue in the temporary deployment state 15' when its temperature is below that of its transition temperature, which can be the temperature of the tissue. Once the element reaches temperature equilibrium with the tissue, it will transform to its permanent engagement state 15 thus capturing the tissue. The element can be removed by lowering its temperature below the transition temperature of the SMA material. This can be achieved by lowering the temperature of the tissue surrounding the element through the application of an external heat sink such as a cold pack. Once the temperature of the element drops below the transition temperature of the SMA material, the SMA material will revert to its martensite phase wherein it is more malleable allowing for the removal of the element. Processing the SMA material such that it has two-way shape memory properties aids in the removal process. Two-way shape memory is the ability of a shape memory alloy to recover a secondary set shape upon cooling from temperatures above the transition temperature of the SMA material. Hence, the element would form its permanent engagement shape 15 when the SMA material is above its transition temperature, and then the element would revert to its temporary deployment state 15' when cooled below the transition temperature of the material. A method for two-way shape memory processing is shape memory cycling. Shape memory cycling involves repeatedly cooling, deforming, and heating the SMA material in the two desired configurations (for example the permanent engagement 15 and temporary deployment 15' shapes in FIGS. 2B and 2C respectively). Other forms of two-way shape memory processing include constrained temperature cycling and constrained aging for long periods of time.

Figure 2D:
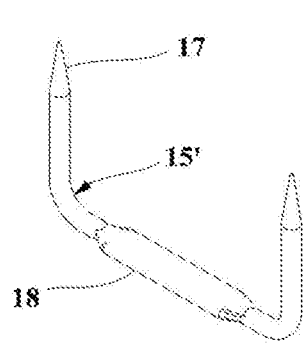
Figure 2E:
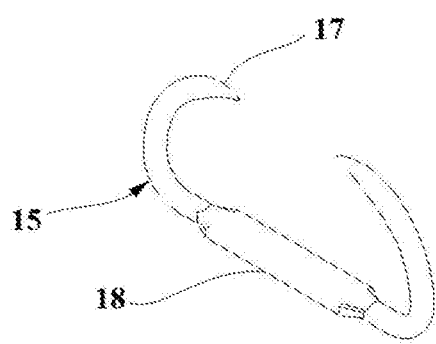

FIG. 2D shows an alternative embodiment of the SMA material tissue capture element in its engagement state 15'. As shown in FIG. 2D a flange 18 is added to the base of the tissue capture element by initial shaping of the material or flattening of the base during mechanical processing of the arms. FIG. 2D also shows the addition of beveled tips 17 to the arms 14 of the element. The beveled tips allow for the easy penetration of the arms into the target tissue. The beveled tips on the elements can be achieved through a variety of methods including mechanical grinding or the chemical removal of the tip material. FIG. 2E shows the SMA tissue capture element in its permanent engagement state 15.

Figure 3A:
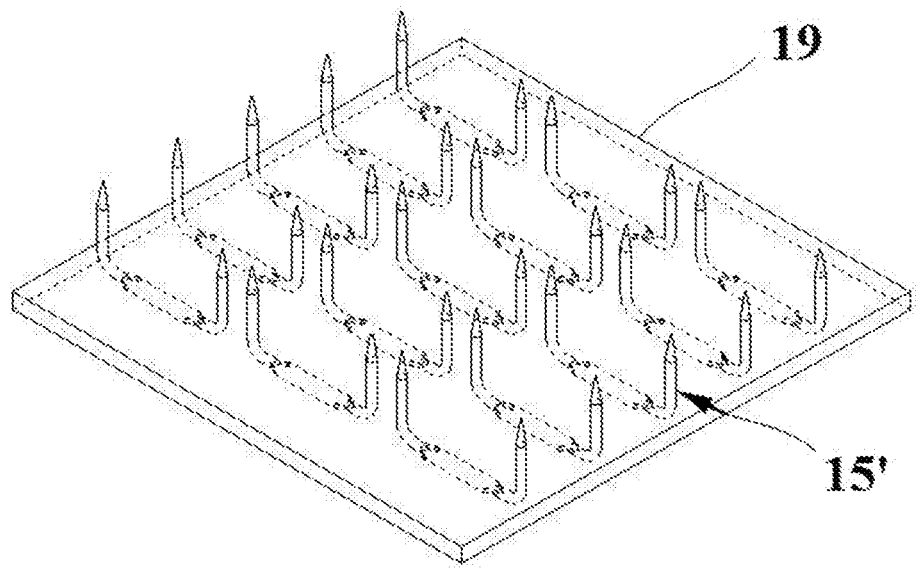
FIGS. 3A and B show shape memory alloy elements created via the processing in FIGS. 2A-E formed into flexible base material.
Figure 3B:
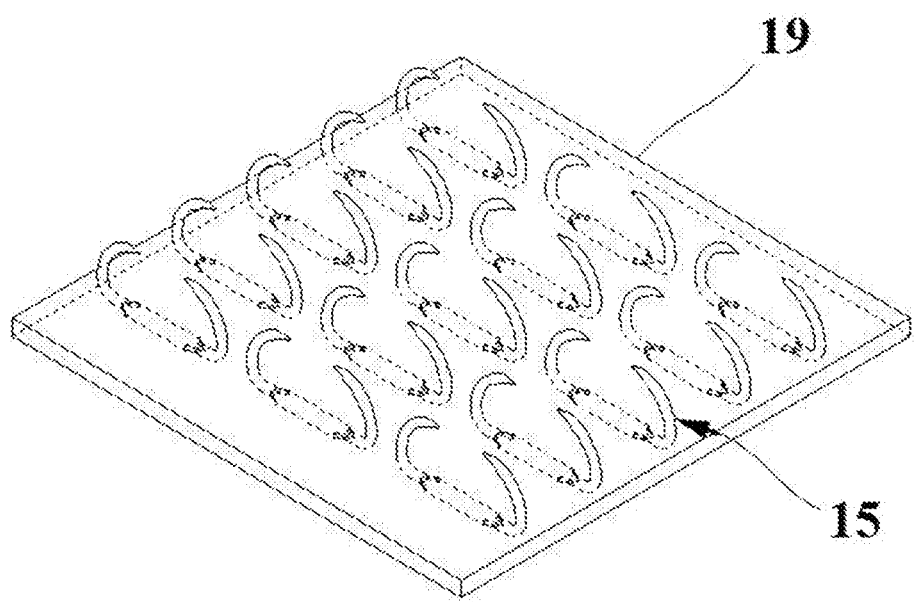
Figure 4A:
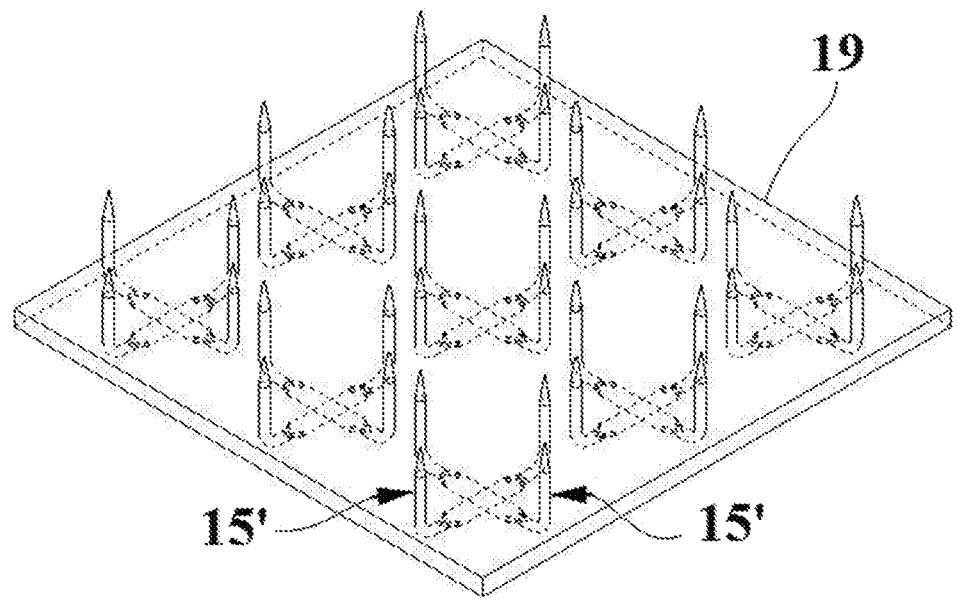
FIGS. 4A and B show the shape memory alloy elements created via the processing in FIGS. 2A-E formed into flexible base material in a cross hatch pattern.
Figure 4B:
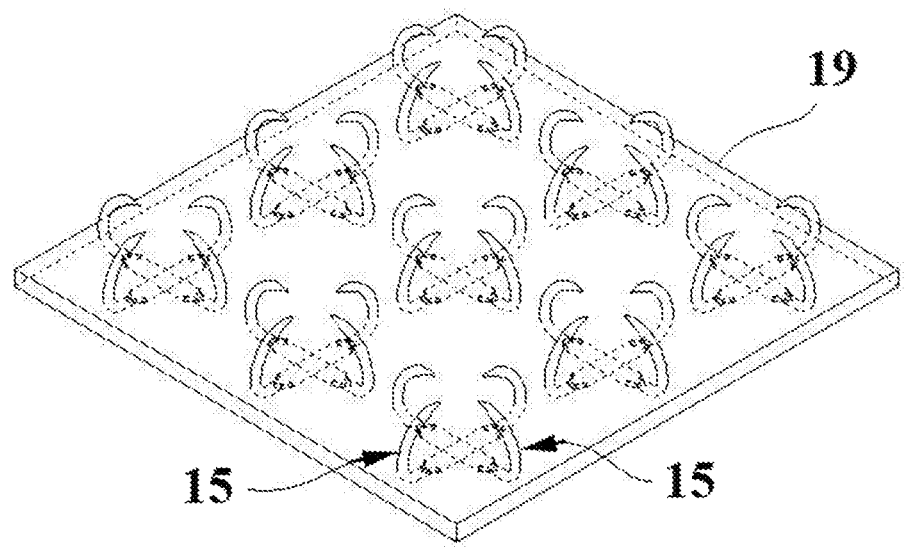

FIG. 3A shows an embodiment of a tissue capture pad that incorporates the SMA tissue capture elements. An array of tissue capture elements with added flanges in the temporary deployment state 15' are molded into a pad of flexible base material 19. It can be seen that the flange 18 widens the base 12 of each element thus increasing the adhesion of the element into the flexible base material 19. The distal ends of the tissue capture elements (the ends which contain the arms 14 and beveled tips 17) can be supported/shielded during the flexible base material overmolding process by inserting them into a suitable array of holes which have been formed into a plate. The plate can consist of any suitable material such as aluminum, and the pattern of support holes could be cut with a laser. After the tissue capture elements have been inserted into the support holes in the plate, the overmolding process can occur via pour molding or injection molding. The overmold process thus covers the flanged sections 18 of the tissue capture elements, while leaving the distal sections 14 and 17 uncovered by the flexible base material 19. FIG. 3B shows the array of tissue capture elements in their permanent engagement state 15. In another embodiment of the pad, as shown in FIG. 4A, an array of tissue capture elements in the temporary state 15' are molded in a cross hatch pattern into a pad of flexible base material 19. FIG. 4B shows the cross hatched array of tissue capture elements in their permanent engagement state 15. While shown as symmetrical evenly spaced arrays in the embodiments of FIGS. 3A, 3B, 4A and 4B, uneven spacing or varied symmetry arrays may be employed in alternative embodiments. It should also be noted that the scale of the tissue capture elements is greatly exaggerated in the FIGS. 3 and 4 in order to make then clearly visible in the figures.

Shape Memory Polymer (SMP) materials provide a multitude of design possibilities for the tissue capture elements. Like Shape Memory Alloys, Shape Memory Polymers have the ability to change their shape with the application of an external stimulus. External stimuli can include the application of thermal energy, the application of light in the form of laser energy or Ultra violet (UV) sources, the application of current, or a pH change of the material surrounding the SMP material. For thermally activated SMP's, there are two important temperature demarcations. The first is the permanent temperature (Tperm), above which the polymer melts and can be formed into its permanent shape through various processes which include molding, extrusion, rolling, thin film deposition, and other similar processes. The second important temperature which is important to the processing of SMP's is the Transition temperature (Ttrans). SMP's are typically block copolymers, and Ttrans is usually the melting temperature or glass transition temperature of one of the block polymers. Temporary shapes can be fixed in SMP's by applying an external stress to the material and then heating to a temperature above Ttrans but below Tperm for a specific period of time. The material is then allowed to cool, and the temporary shape is set. When the material is heated above Ttrans, the material reverts to its permanent shape. The shape transition is due to entropy elasticity within the polymer chains, that is the most favored state of entropy for a molecular chain is a random tightly wound coil (as opposed to a straight chain). When an external stress is applied to an SMP material heated above Ttrans, the molecular chains straighten and are then subsequently "frozen" into place when the material is cooled below Ttrans. When the material is again heated above Ttrans, the chains are free to move and the material reverts to its permanent shape.

In the case of light activated shape memory polymers, the temporary shape of the material is fixed by the application of light at a certain wavelength (w1). That forms crosslinks between the polymer chains. When light at a different specific wavelength (w2) is applied, the crosslinks between the polymer chains are broken and the material reverts to its permanent shape via entropy elasticity. The following shape memory polymer embodiments can be activated by thermal, light, current, or chemical means. Thermal activation is used as a specific example in each case for illustrative purposes.

Figure 5A:
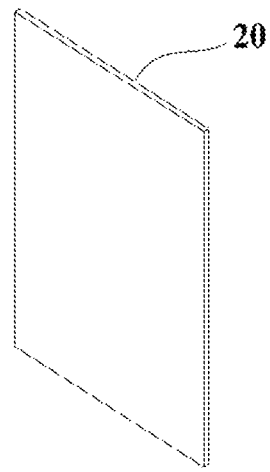
FIGS. 5A-F show a method for the formation of a one way deflectable composite shape memory polymer element.
Figure 5B:
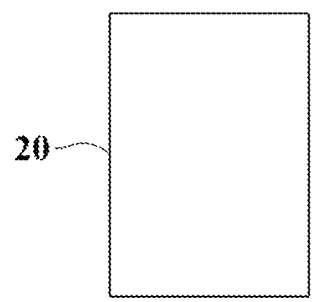
Figure 5B:
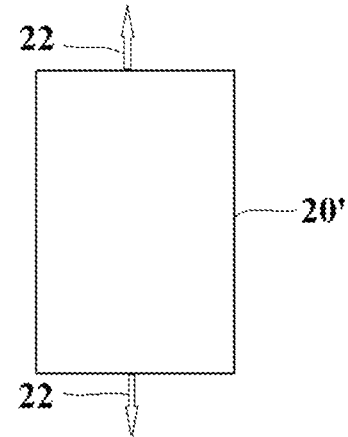
Figure 5C:
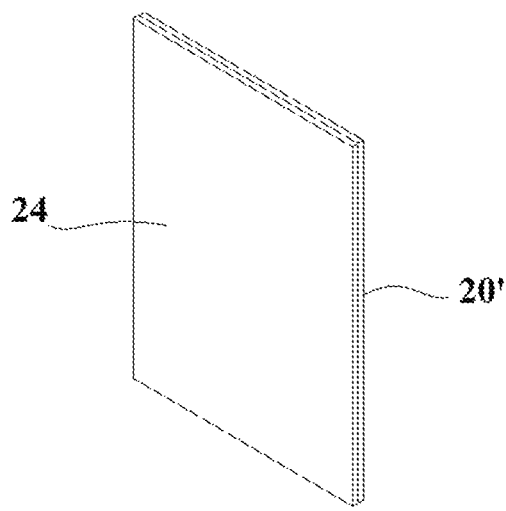
Figure 5D:
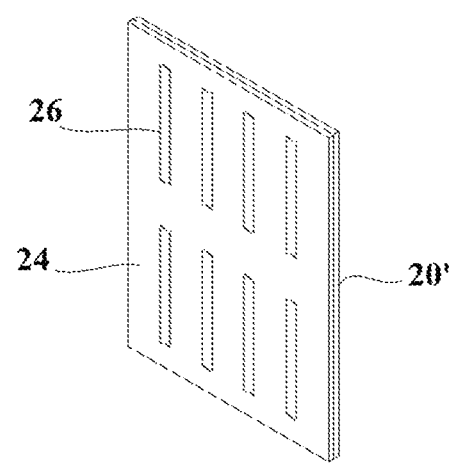
Figure 5E:
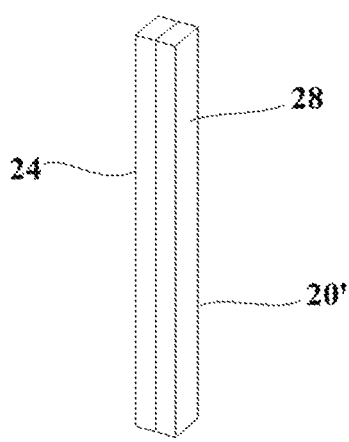
Figure 5F:
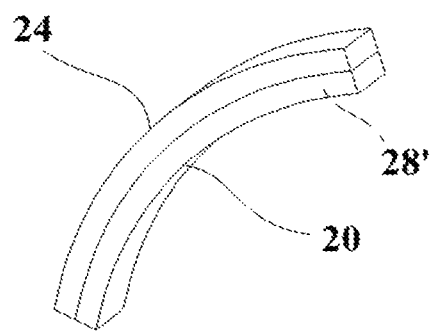
Figure 20A:
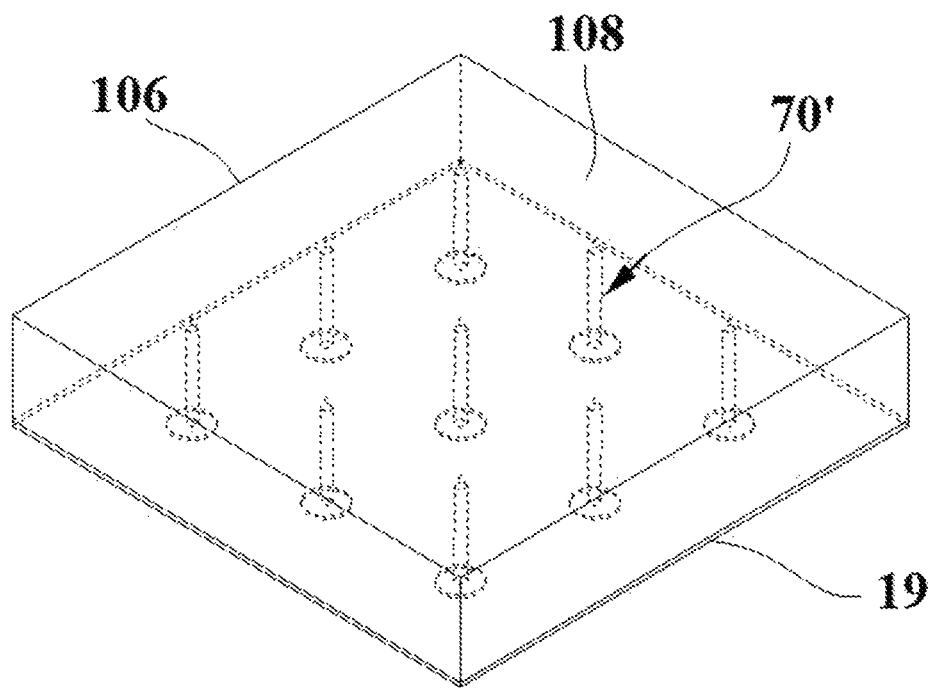
FIGS. 20A-F depict the addition of a thermally insulation foam to the tissue capture element/flexible base material assembly; and, FIGS. 21A and B depict a shape memory alloy element activated into a deflected shape by the application of electro magnetic energy.
Figure 20B:
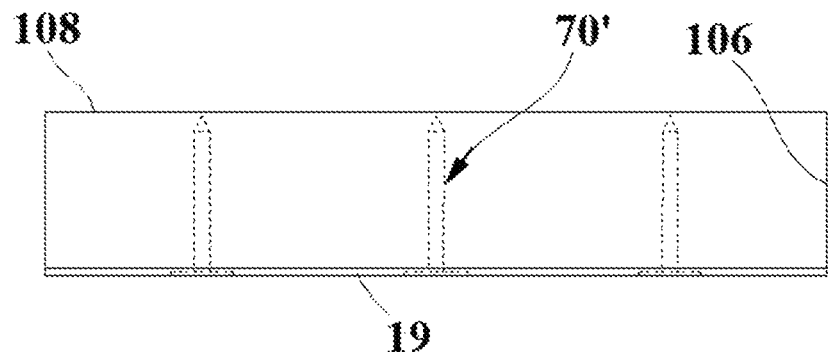
Figure 20C:
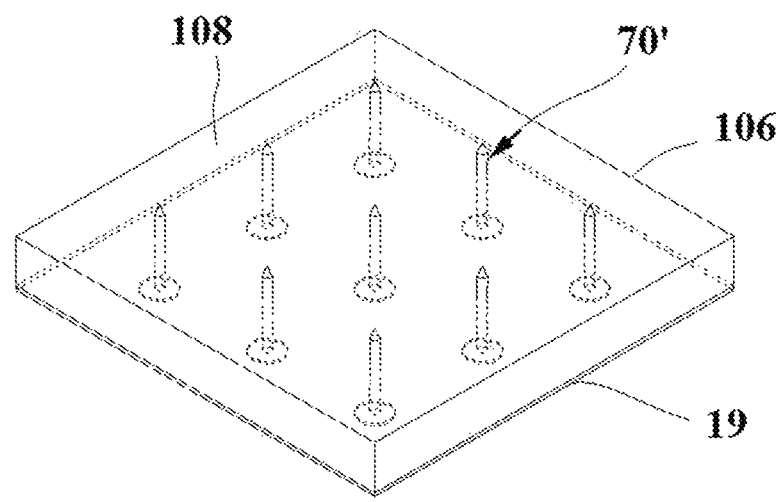
Figure 20D:
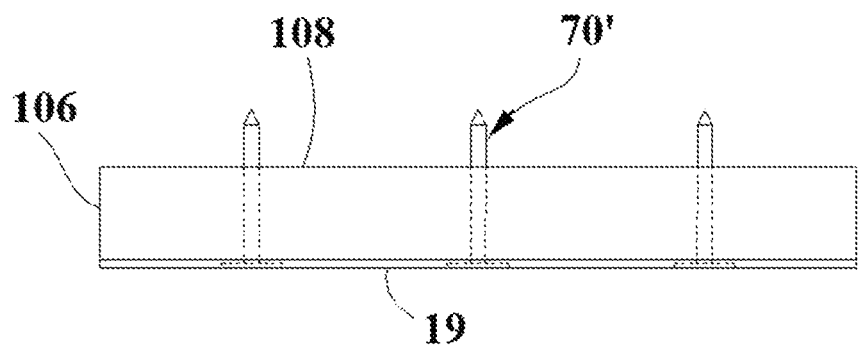
Figure 20E:
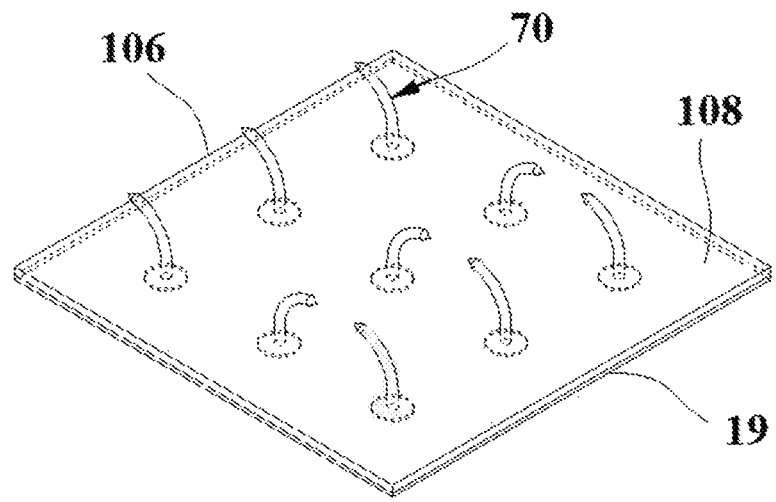
Figure 20F:
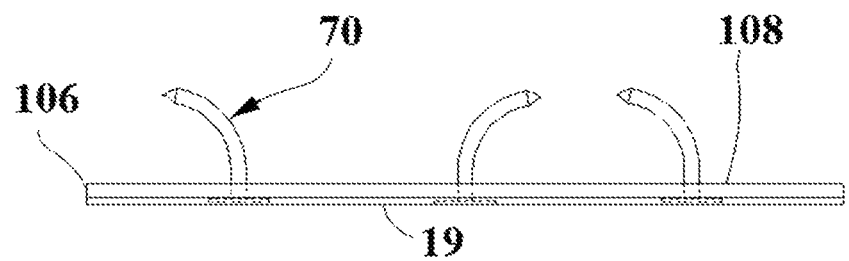

FIG. 5A shows a sheet of shape memory polymer material 20. The transition temperature of the material is defined to be Ttrans1. FIG. 5B shows that sheet of material before and after the application of an external stress 22 which elongates the material to state 20' as shown in the figure. The external stress is applied while the temperature of the material is greater than Ttrans1. The material can then be cooled to a temperature below that of Ttrans1 thus setting the temporary elongated shape 20' in the material. FIG. 5C shows the elongated SMP sheet 20' bonded or fused to a sheet of standard polymer material 24. In this case, each SMP sheet would have the same thickness, although the thickness of each sheet could vary in other embodiments. The bonding/fusion of the two sheets can be achieved through the use of a suitable adhesive such as Loctite® 4206 or 3M™ Plastic Bonding Adhesive 2665. FIG. 5D shows cut lines 26 in the composite sheet. The cut line pattern can be created in the sheet through the use of laser cutting, e-beam cutting, or mechanical stamping. When the material within the cut line pattern is removed, is comprises the composite sheet element 28 that is shown in FIG. 5E. The shape of the composite element 28 shown it the drawings is not conducive to tissue capture; it is used here to demonstrate the deflection capabilities of a SMP composite sheet element. When the composite element is heated above the transition temperature Ttrans1, the SMP material reverts to the unstrained shape 20 shown in FIG. 5B. The temperature has no effect on the standard polymer 24, thus the "shrinking" of the SMP material from 20' to 20 causes the composite element to deflect to state 28' as shown in FIG. 20F. The composite sheets described herein are formed from polymer materials. In alternative embodiments, foil or thin sheets of shape memory alloys may be employed.

The following approximates the amount of deflection of the composite sheet element 28 for a set of parameters for the described embodiment. For an exemplary embodiment, the temporary shape setting process shown in FIG. 5D has induced a temporary strain of 0.15 on the SMP material 20'. Also for that embodiment, the length of the element 28 is 1 mm. The thickness of each polymer sheet for the embodiment as described is 0.05 mm. The length that the 1 mm section of SMP material 20' will thus recover is:

$$\Delta L = \varepsilon * L_0 = 0.15 * 1 \text{ mm} = 0.15 \text{ mm}$$

Figure 6A:
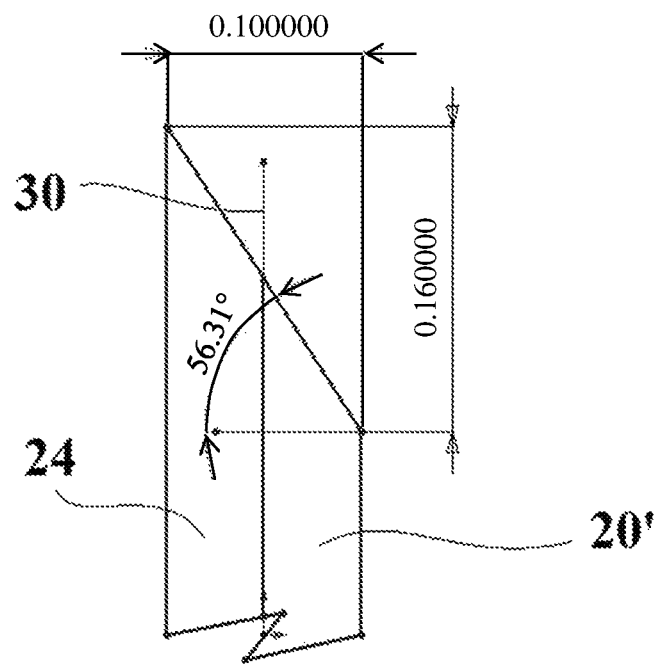
FIGS. 6A and B depict a calculated deflection for the composite shape memory polymer element shown in FIGS. 5A-F.

As shown in FIG. 6A (all dimensions in mm), a decrease of 0.15 mm in the length of the SMP material 20' with the given sheet thicknesses will lead to a deflection of:

$$\theta = a\tan\left(\frac{0.15 \text{ mm}}{1 \text{ mm}}\right) = 0.9826 \text{ rad}$$

The neutral axis 30 is shown in FIG. 6A. An element of arc length is given by S=r*θ, therefore:

$$r = \frac{S}{\theta} = \frac{1 \text{ mm}}{0.9826 \text{ rad}} = 1.0175 \text{ mm}$$

Figure 6B:
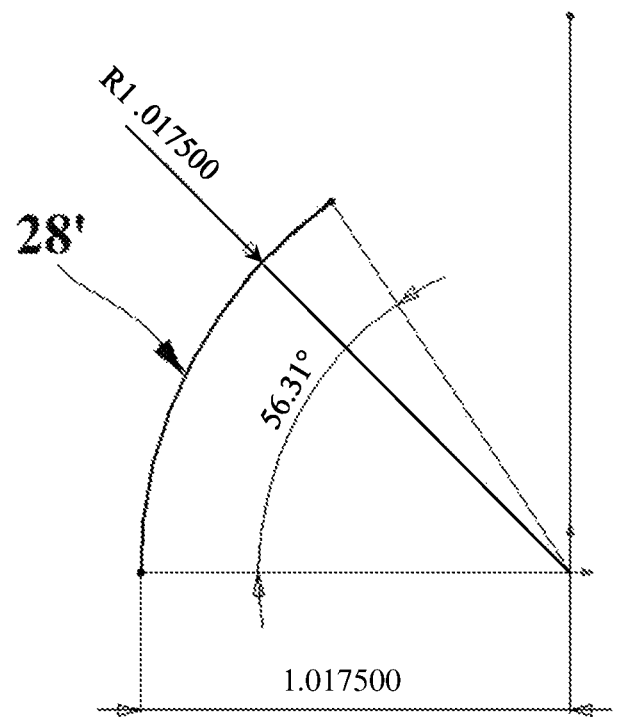

The radius of curvature for the deflected 1 mm element 28' is shown in FIG. 6B. Of course, the amount of deflection and the radius of curvature would vary for elements of different dimensions and SMP material with different amounts of strain.

Figure 7A:
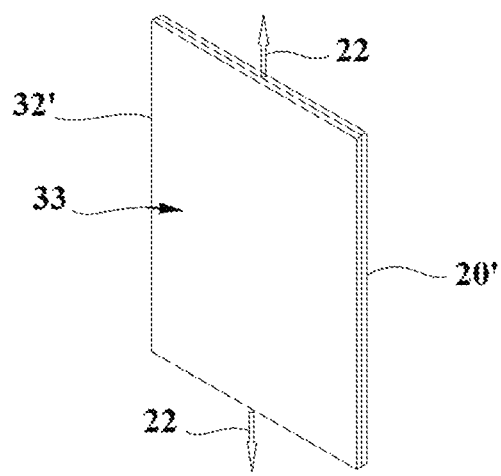
FIGS. 7A-E show a method for the formation of a two way deflectable composite shape memory polymer element.
Figure 7B:
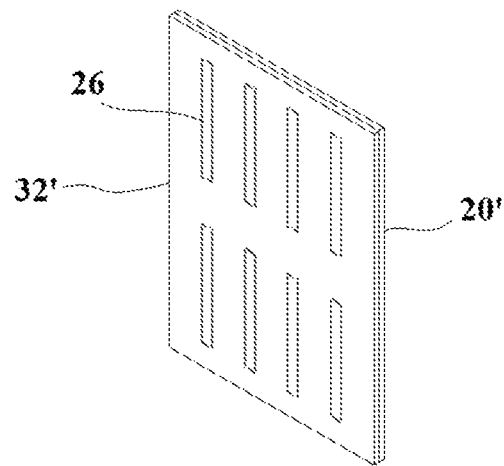
Figure 7C:
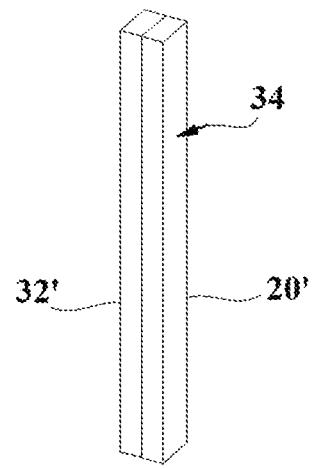
Figure 7D:
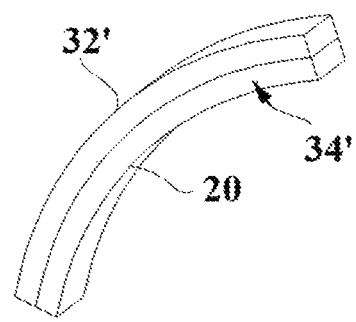
Figure 7E:
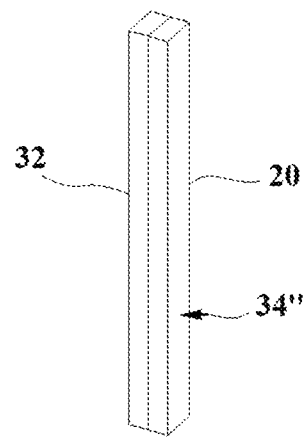

FIG. 7A shows two SMP material sheets 20 and 32 with two different transition temperatures comprising a composite sheet 33 which undergoes a temporary shape setting process. For an exemplary embodiment, SMP material sheet 20 has a transition temperature of Ttrans1, and SMP material sheet 32 has a transition temperature of Ttrans2. In this case, each SMP sheet would have the same thickness, although the thickness of each sheet could vary in other embodiments. The two sheets of SMP material 20 and 32 can be thermally fused or bonded together. An external stress 22 can then be applied to the composite sheet 33 while the sheet is held at a temperature above both Ttrans1 and Ttrans2. Each material can then be cooled below its transition temperature thus setting temporary "stretched" shapes 20' and 32' into the two materials which form the composite sheet 33. Composite elements 34 shown in FIG. 7C can then cut from the composite sheet via the cut lines 26 shown in FIG. 7B. The shape of the composite element 34 shown in the drawings is not conducive to tissue capture; it is used here to demonstrate the dual deflection capabilities of the dual SMP composite sheet element. FIG. 7D shows the composite element 34' after the element has been heated past Ttrans1 thus activating SMP material 20' and causing it to transition to its unstrained state 20. The composite element 34' is thus deflected in the direction of SMP material 20 as shown in FIG. 7D. If a temperature greater that that of Ttrans2 is then applied to the composite element 34', the SMP material 32' will transition to its unstrained state 32, and the SMP composite element will revert to the configuration 34" shown in FIG. 7E. This process thus allows for the reversible activation of the element. As an example Ttrans1 is set at body temperature 37° C., and Ttrans2 is set to 45° C. a temperature below which tissue necrosis typically occurs, 50° C. Also for the described embodiment, the shape of the dual SMP element 34 is altered, as will be described subsequently, to be conducive to insertion into tissue. The composite element 34 is inserted into the tissue in the "deployment" state 34 and SMP material 20' is activated by the temperature of the tissue 37° C. thus returning it to its unstrained state 20. The SMP composite element will then be deformed to an "engagement" state 34' as shown in FIG. 7D. If an external heat source at 45° C. is then applied to the tissue in order to heat it, SMP material 32' will return to its unstrained state 32 and the dual SMP composite element will assume the "removal" state 34" shown in FIG. 7E.

Figure 8A:
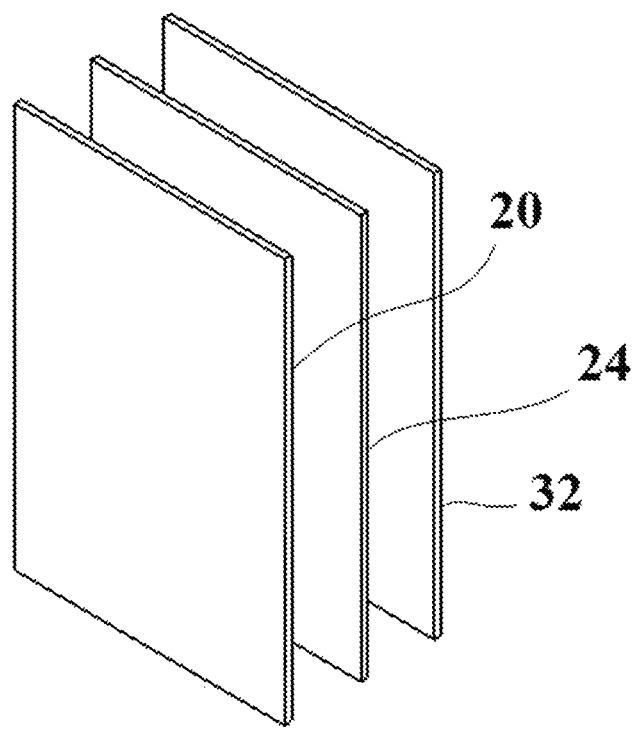
FIGS. 8A and B depict a multi-layer composite sheet suitable for creating shape memory polymer tissue capture elements of any configuration.
Figure 8B:
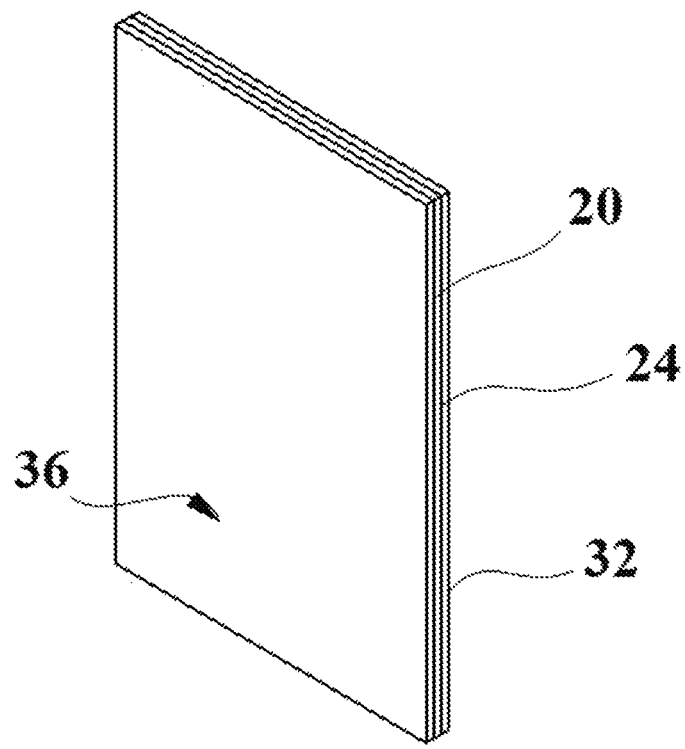

FIG. 8A shows a composite sheet with multiple layers. In this case the two outer layers 20 and 32 are SMP material, and the inner layer 24 is a standard polymer material. FIG. 8B shows the three layers bonded or fused together to form the composite sheet 36. The central layer 24 provides a neutral surface to facilitate the deformation of the resulting elements cut from the sheet. The central standard polymer layer 24 may also have a much higher durometer than the two surrounding layers 20 and 32, thus making it much stiffer than the outer two SMP layers. This would serve to increase the overall stiffness of the resulting elements cut from the sheet, thus allowing for easier insertion into the target tissue. The central layer could also be a metal such as superelastic Nitinol. Although three layers of composite polymer materials are shown in FIGS. 8A and 8B, any possible combination of the number of sheets, order of the sheets, and materials that comprise the sheets could be used in order to form the composite sheet.

Figure 9A:
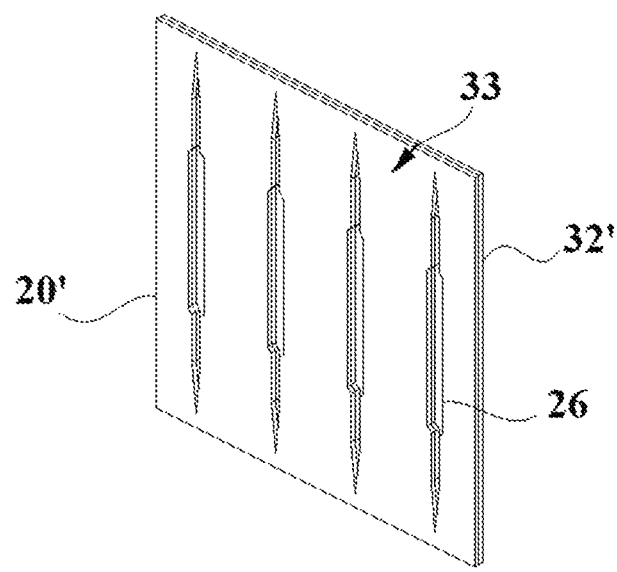
FIGS. 9A-E show the creation of a shape memory polymer tissue capture element from a dual shape memory polymer sheet.
Figure 9B:
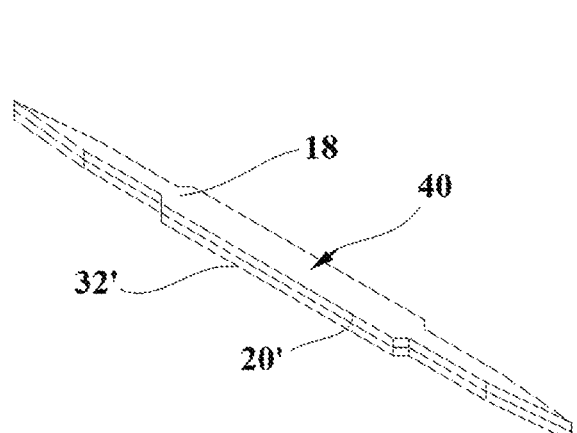
Figure 9C:
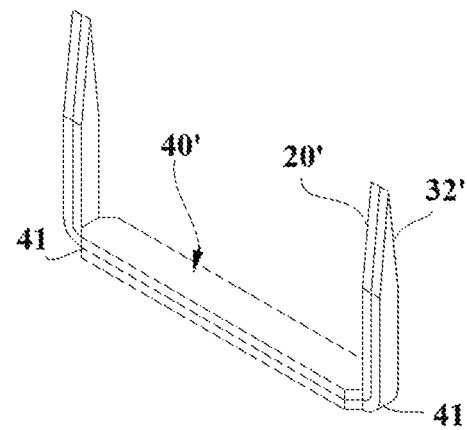
Figure 9D:
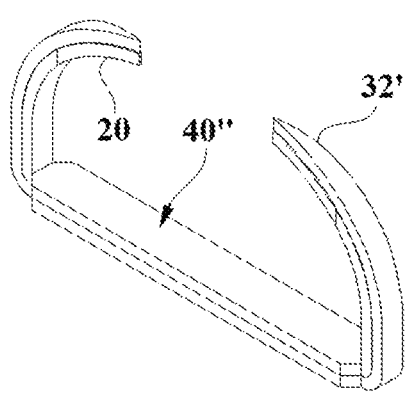
Figure 9E:
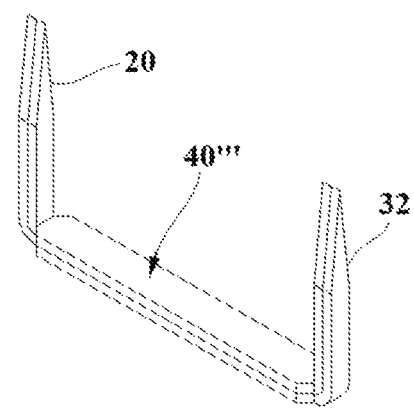

A method for formation and use of an SMP tissue capture element embodiment with the deployment-engagement-removal activation capabilities that have previously been described is shown in FIGS. 9A-9E. FIG. 9A shows a SMP composite sheet 33 formed from two SMP material sheets 20 and 32 with transition temperatures Ttrans1 and Ttrans2 respectively. The composite sheet 33 is processed as previously described such that each sheet is in pre-strained states 20' and 32'. A pattern for a tissue capture element is cut along the cut lines 26 which provide shaping for a flange 18 as previously described for the first embodiment and pointed tips for piercing tissue. The resulting tissue capture element 40 is shown in FIG. 9B. The tissue capture element 40 is flat as cut from the composite sheet, and must be suitably configured to facilitate penetration into the target tissue. To accomplish this, the SMP tissue capture element can be placed over a form and heat applied to the transition areas indicated with element 41 in FIG. 9C. The element would then be allowed to cool over the form, and this would result in the SMP tissue capture element deployment configuration 40' shown in FIG. 9C. FIG. 9D shows the resulting SMP tissue capture element at a temperature of Ttrans1 thus having transitioned SMP material 20' to its unstrained state 20, and configuring the tissue capture element in its tissue engagement state 40". FIG. 9E shows the resulting tissue capture element at temperature of Ttrans2 thus having transitioned SMP material 32' to its unstrained state 32, and configuring the SMP tissue capture element in its removal state 40'".

Figure 12B:
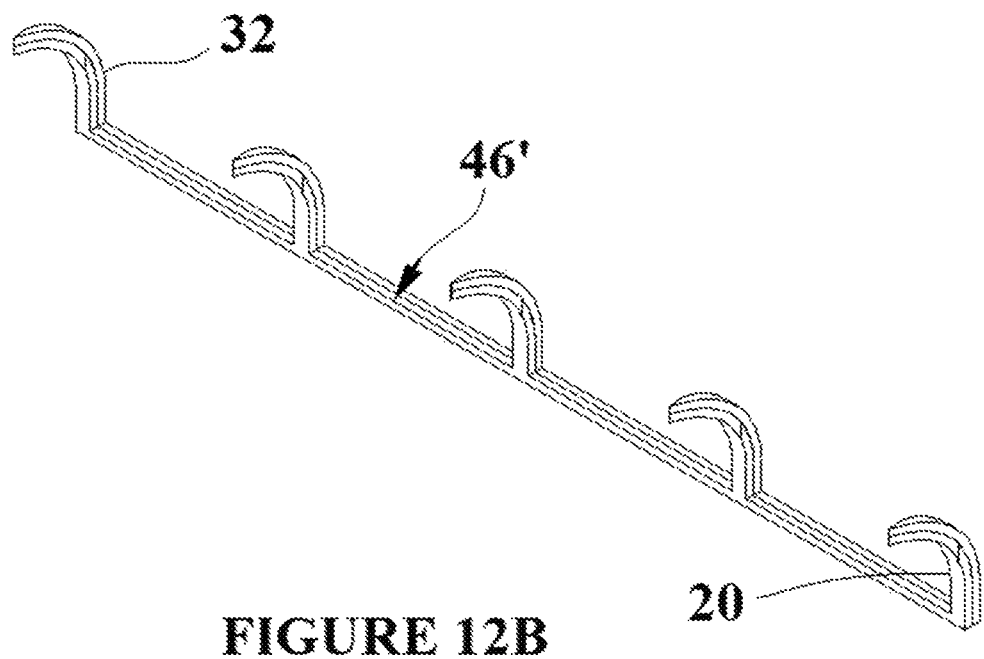
FIGS. 12A and B show a multiple shape memory polymer tissue capture element created from a dual shape memory polymer sheet.
Figure 13:
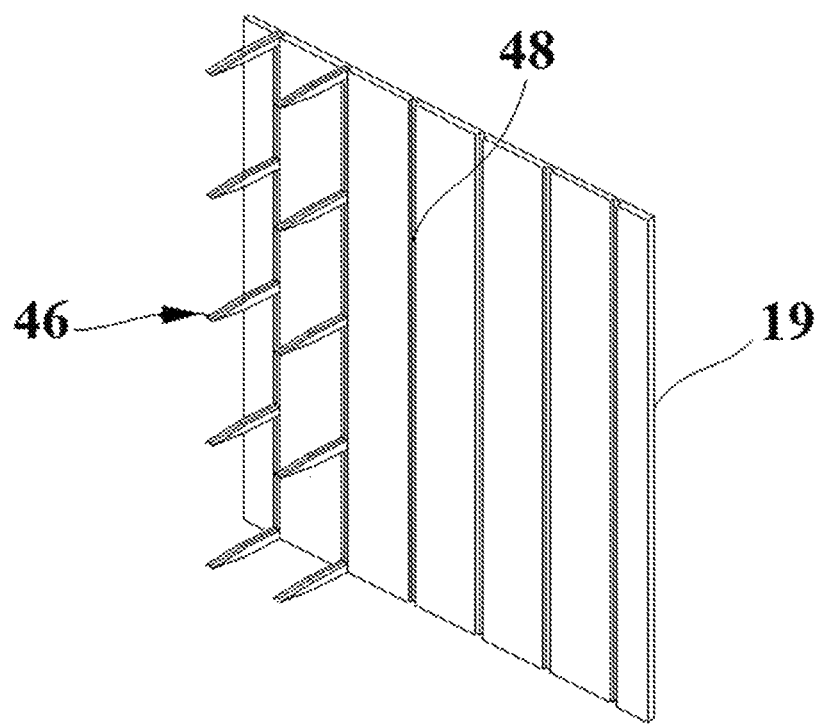
FIG. 13 shows the multiple shape memory polymer tissue capture element shown in FIGS. 12A and B inserted into flexible base material.

FIG. 10A shows another embodiment of a tissue capture element cut from a duel SMP composite sheet such as sheet 33 shown in FIG. 7A having a pointed tip for piercing tissue and a base 43 comparable in function to the flange of the prior embodiment for enhanced retention in a mold substrate as will be describe subsequently. The composite tissue capture element 42 shown in the deployment state is comprised of two pre-strained SMP polymer materials 20' and 32' (Ttrans1 and Ttrans2 respectively) which allow for the deployment-engagement-removal state transitions which have been previously described. The SMP composite shape memory element is shown above Trans1 in the engagement state 32' in FIG. 10B with the SMP material 20' transitioned to its unstrained state 20. The SMP composite shape memory element is shown above Trans2 in the removal state 42" in FIG. 10B with the SMP material 32' transitioned to its unstrained state 32. FIG. 11A shows a double version 44 of the composite tissue capture element 42 shown in the deployment state FIG. 10A. The double composite elements are shown in the engagement state in FIG. 11B with the SMP material 20' transitioned to its unstrained state 20. FIG. 12A shows a multiple tipped version 46 of the composite tissue capture element 42 shown in the deployment state similar to FIG. 10A. The embodiment of FIG. 12A employs a spine 47 interconnecting the tips for adherence into a substrate. The multiple composite elements are shown in the engagement state 46' in FIG. 12B with the SMP material 20' transitioned to its unstrained state 20. FIG. 13 shows the multiple composite element embodiment 46 in the deployment state with spine 47 placed into slots 48 in a pre-formed section of flexible base material 19. The scale of the multiple composite elements is exaggerated in FIG. 13 in order to make them clearly visible.

Figure 14A:
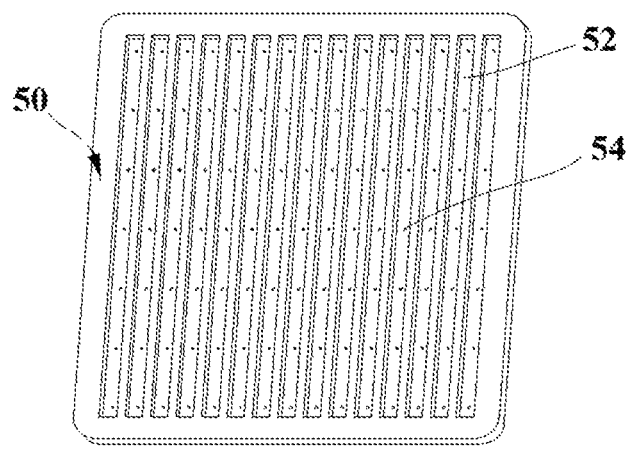
FIGS. 14A-I depict the simultaneous formation of an array of shape memory polymer elements through a vacuum forming process. The array is then molded into flexible base material.
Figure 14B:
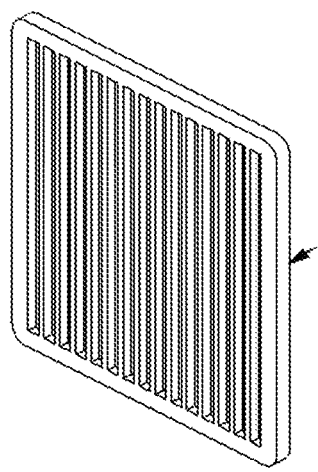
Figure 14C:
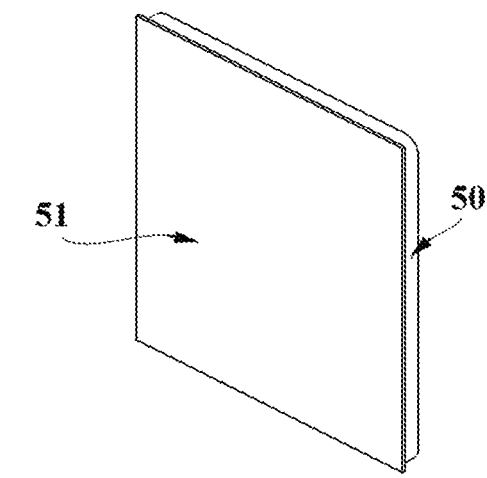
Figure 14D:
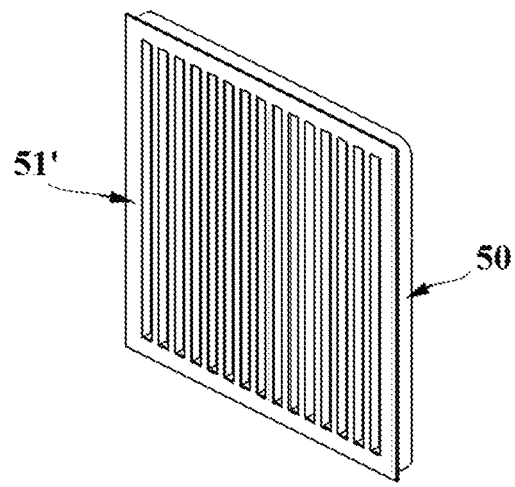
Figure 14E:
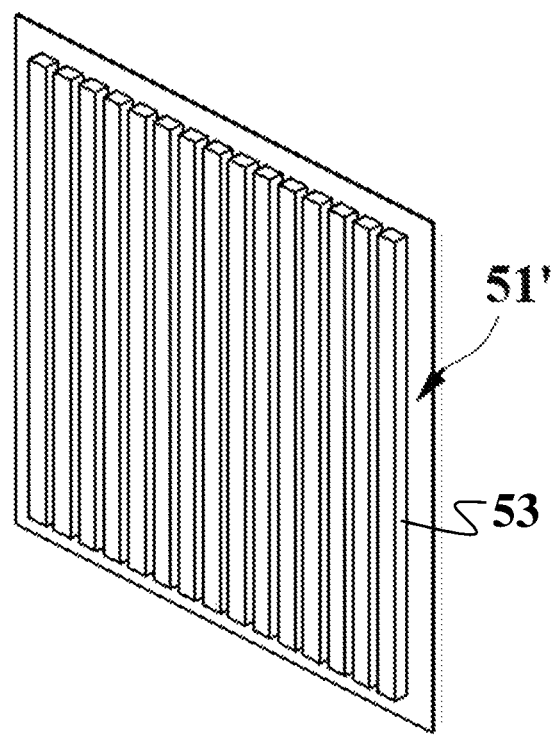
Figure 14F:
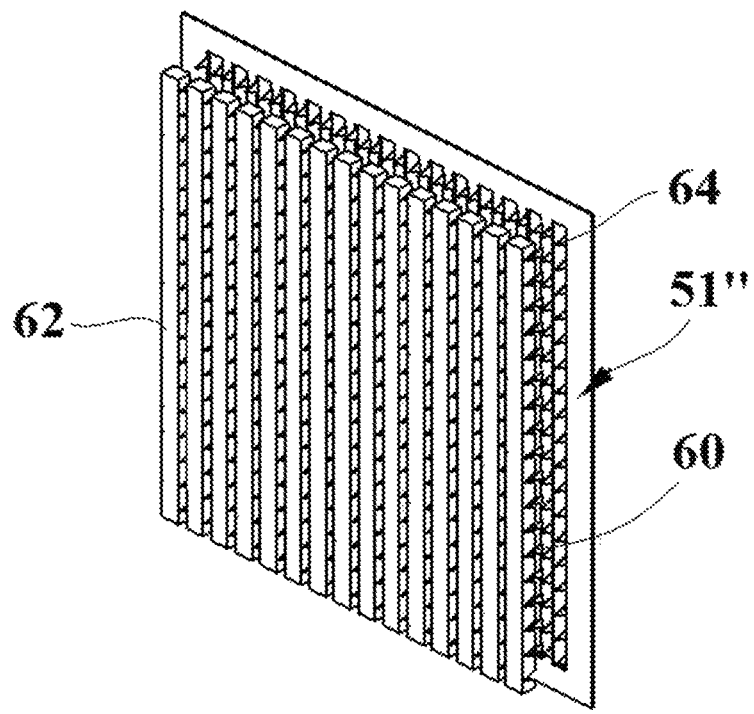
Figure 14G:
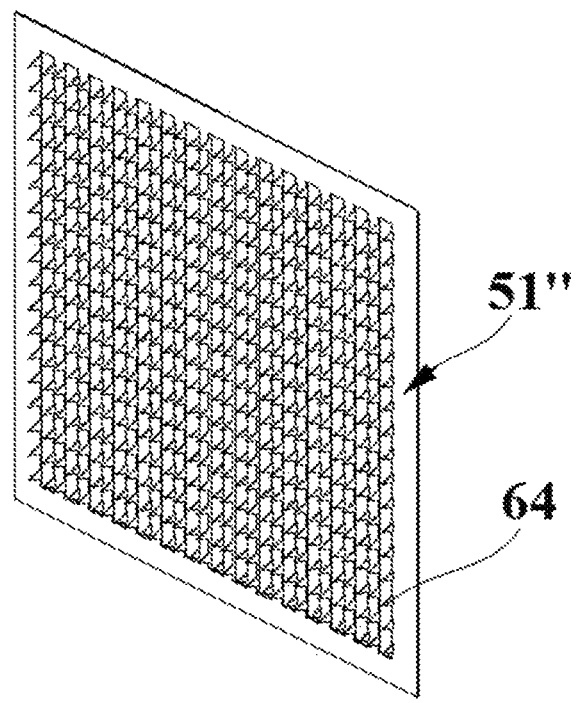
Figure 14H:
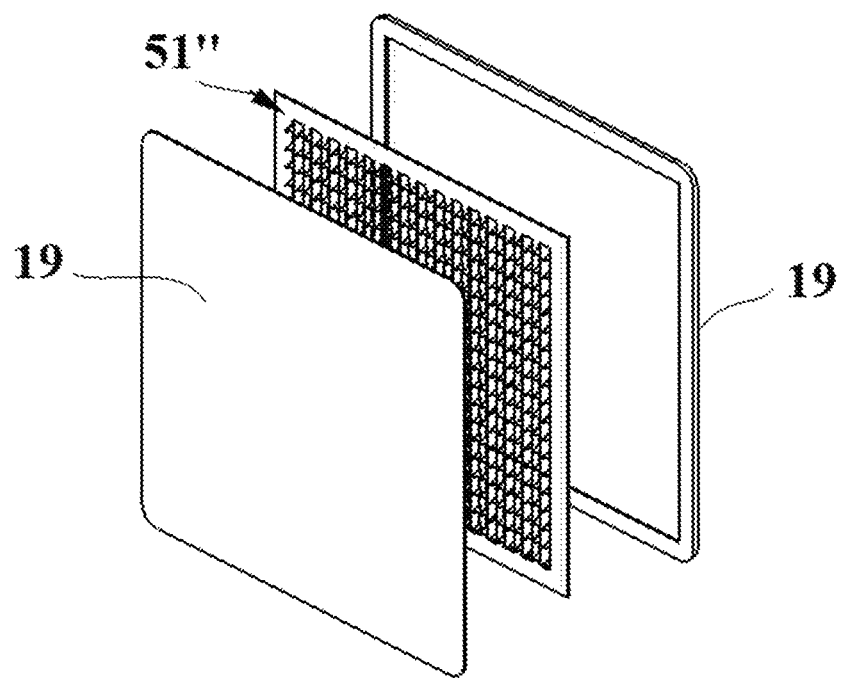
Figure 14I:
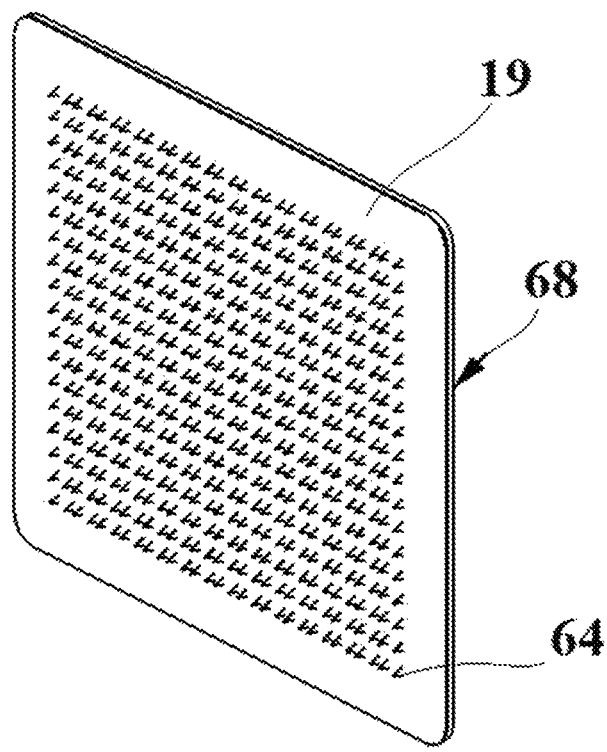

The ability to manufacture multiple SMP tissue capture elements simultaneously while limiting the number of processing steps is desirable. To that end, FIG. 14A depicts a vacuum form mold 50, which contains slots 52 and vacuum holes 54. The mold allows for the forming of an unstrained duel SMP composite sheet 51 such that multiple tissue capture elements can be cut from the formed SMP composite sheet. FIG. 14C shows an un-strained duel SMP composite sheet 51 comprised of two SMP sheets (20 with Ttrans1 and 32 with Trtrans2) placed on the face of the vacuum mold 50. In FIG. 14D, the mold 50 and SMP composite sheet 51 are heated to a temperature above Ttrans2, and then a vacuum is applied to the sheet via the vacuum holes 54. Sections of the composite sheet 51 are pulled into the slots 52 of the mold when the vacuum is applied creating the formed sheet 51' having corrugated sides 53. The mold 50 and formed SMP composite sheet 51' can then cooled to a temperature below Ttrans1, and the formed sheet can be removed from the mold. The formed SMP composite sheet 51' is shown in FIG. 14E. FIG. 14F shows a pattern of tissue capture elements 64 in the deployment state being cut from the formed SMP composite sheet 51' along cut lines 60 perpendicular to the corrugated sides to create the formed cut SMP composite sheet 51". The cuts in the formed and cut composite sheet 51" can be made by laser cutting, e-beam cutting, or mechanical cutting. The excess SMP formed composite sheet material 62 is removed. The vacuum forming process thus acts to set the temporary deployment shape of the elements and sets a uniform strain into each of the composite layers as shown in FIG. 7A. The uniform strain is due to the fact that as the SMP composite sheet 51 is formed into the slots 52, each layer of material is equally stretched as it conforms to the shape of the slot. FIG. 14G shows the formed/cut SMP composite sheet 51" with the resulting tissue capture elements in their deployment state 64. The tissue capture elements 64 will thus have the deployment-engagement-removal state shape transition capabilities described in FIGS. 10A-C due to the vacuum forming process. FIG. 14H is an exploded view showing the formed/cut SMP composite sheet 51" being molded into flexible base material 19. The figure is shown in exploded view, but the molding is a continuous process. The overmold process results in the pad assembly 68 shown in FIG. 14I with tissue penetration tips of the SMP composite protruding from the pad with the linear spines intermediate the tips constrained in the molded base material. Also shown in FIG. 14I are the tissue capture elements 64 in their deployment state, and the flexible base material 19. The scale of the tissue capture elements is greatly exaggerated in FIG. 14I in order that they can be clearly seen in the figure.

Figures 15A, 15B:
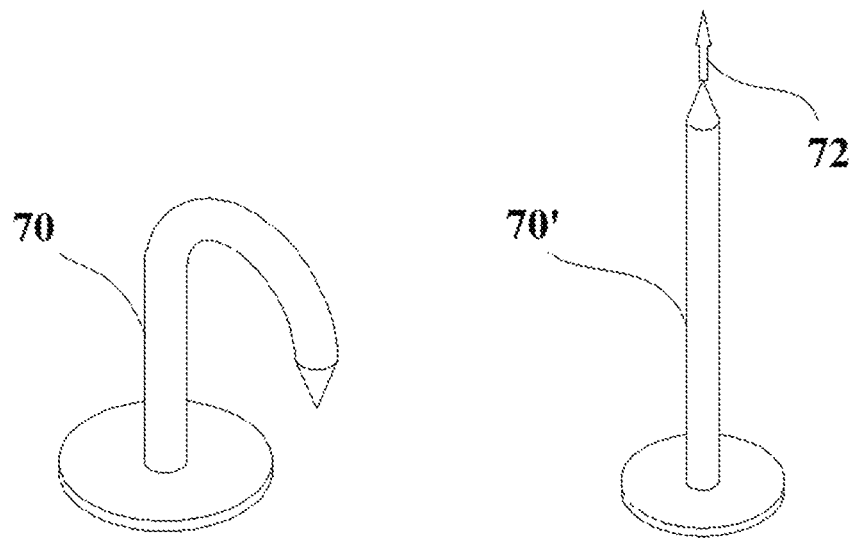
FIGS. 15A and B depict a molded shape memory polymer tissue capture element and its subsequent processing.

FIG. 15A shows a SMP tissue capture element in its engagement state 70 that has been injection molded. The element 70 is molded out of a single SMP material with a transition temperature of Ttrans1. FIG. 15B shows a temporary deployment shape 70' that is set into the element by heating it above its transition temperature Ttrans1, applying an external stress 72 to form the temporary deployment shape 70', and then cooling below the transition temperature Ttrans1. When the element in its temporary deployment shape 70' is heated above its transition temperature Ttrans1, it will return to its permanent engagement shape 70 as shown in FIG. 15A.

A wide variety of surface coatings and surface treatments are available to apply to medical devices and implants. Surface coatings involve processes such as dipping and thin film deposition. Surface treatments involve processes such as plasma etching for alloys and Self Assembling Monolayer End groups (SAMEs) technology for polymers. The surface coatings or surface treatments perform a multitude of functions which include adding lubricity to the surface, adding antimicrobial properties to the surface, adding anesthetic capabilities to the surface, and adding fluid absorption resistance properties to the surface. Any combination of these surface coatings or surface treatments can be added to any given embodiment of the shape memory tissue capture elements and or any given embodiment of the flexible base material. For example, a fluoroploymer coating such as Teflon® can be applied to the surface of Shape Memory Alloy tissue capture elements. This would increase their lubricity and thus ease their insertion into the target tissue. SAMEs technology is a polymer surface treatment that alters the physical properties of the surface of the polymer by utilizing the surface activity and self-assembly in order to control the chemistry and the nano-structure of a polymer's surface. One application of SAMEs technology is to limit the absorption of fluids by the polymer, which can degrade the shape memory properties and stiffness of SMP materials. An anesthetic coating such as Xylocaine® or Hurricaine® could be applied to any embodiment of tissue capture element and or flexible base material in order to reduce pain upon insertion into the target tissue. An antimicrobial coating which contains silver oxide could be applied to any embodiment of the tissue capture elements and or any embodiment of the flexible base material in order to reduce the possibility of infection at the wound site.

Figure 16A:
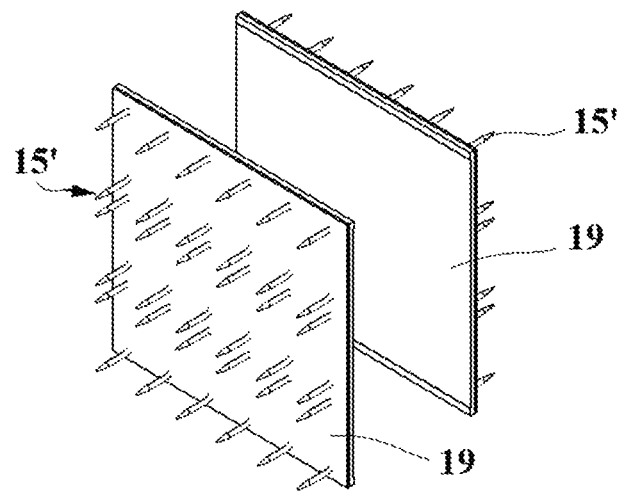
FIGS. 16A-D depict a double sided tissue capture element/flexible base material assembly where the tissue capture elements are on both sides of the flexible base material.
Figure 16B:
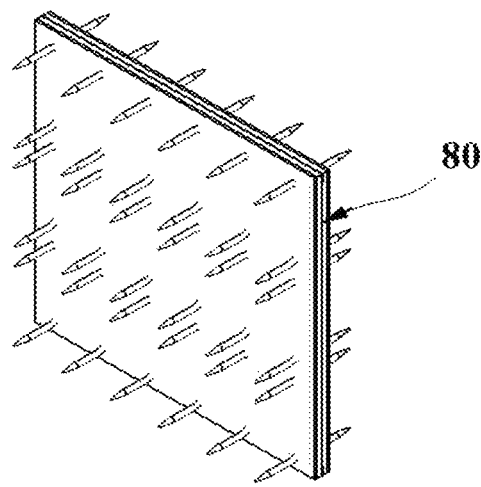
Figure 16C:
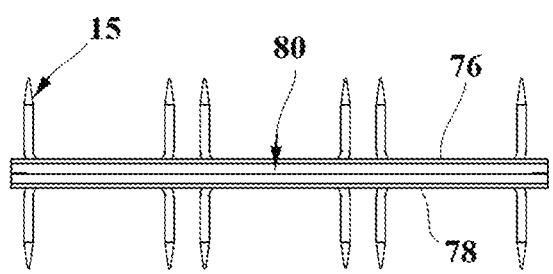
Figure 16D:
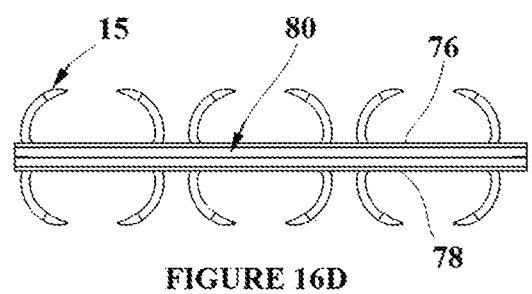

All embodiments of the tissue capture elements and flexible base material that have thus been described involve the tissue capture elements on one surface only of the flexible base material. FIG. 16A depicts two surfaces comprised of flexible base material 19 and tissue capture elements in their deployment state 15' (as shown in FIG. 2D) joined together to form the composite surface 80 with tissue capture elements on both sides shown in FIG. 16B. FIGS. 16C and 16D show a cross sectional view of the surface with the shape memory tissue capture elements in the temporary deployment 15' and permanent engagement 15 states respectively. This surface arrangement could be configured in the form of a pad which could be used to close a wound as described by the following. The composite two sided pad 80 could be deployed into the target tissue such that the target tissue was flush with surface one 76 and simultaneously flush with surface two 78. The tissue capture elements could then be activated to their permanent engagement state 15 as shown in FIG. 16D. This would effectively adhere the target tissue to both surfaces 76 and 78 of the composite two sided pad 80. The scale of the tissue capture elements is greatly exaggerated in FIGS. 16A-16D in order that they can be clearly seen in each figure.

Figure 17A:
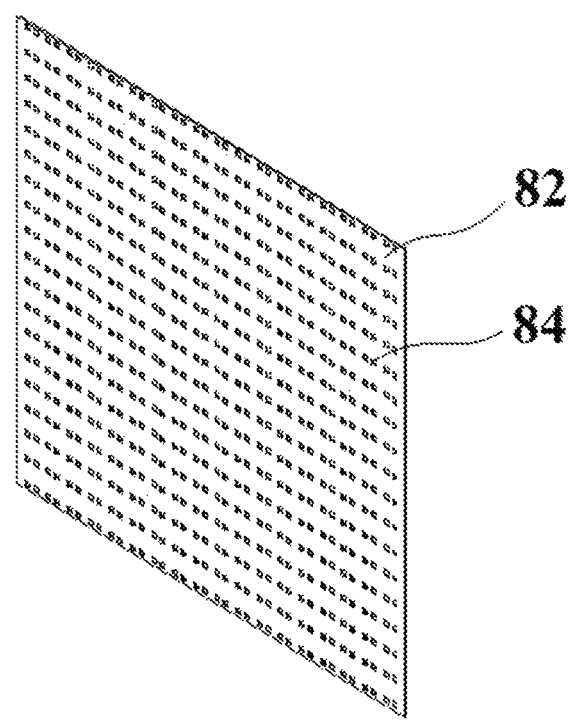
FIGS. 17A-E depict the formation of a tissue capture element/flexible base material assembly with an integrated mesh that supports the tissue capture elements.
Figure 17B:
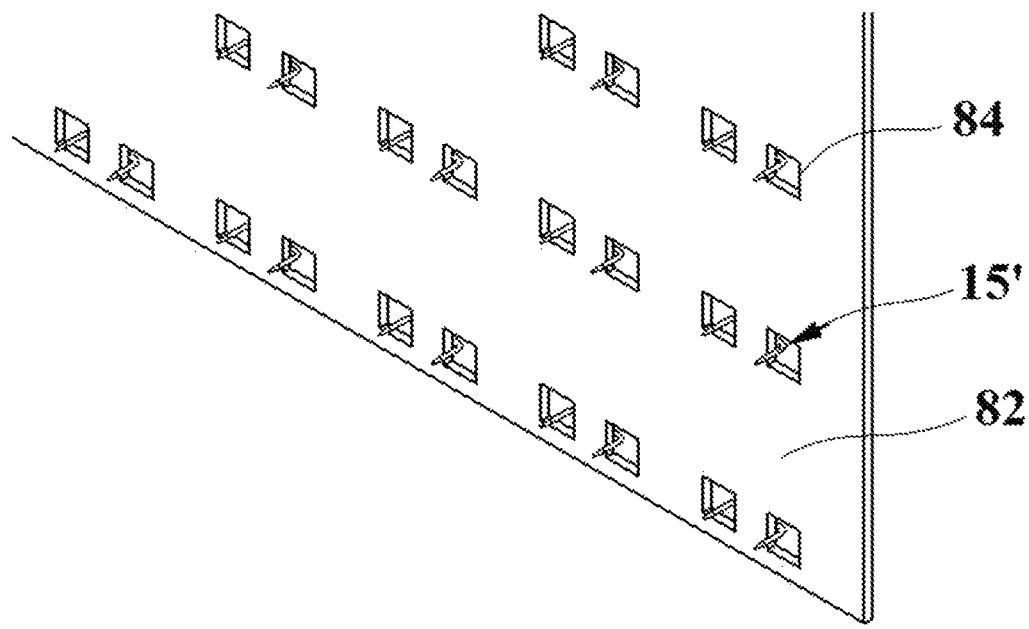
Figure 17C:
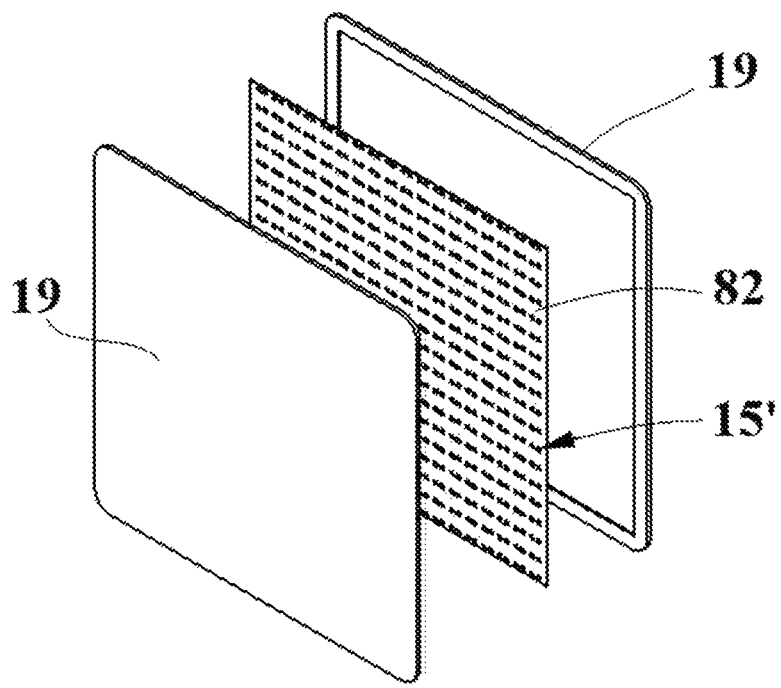
Figure 17D:
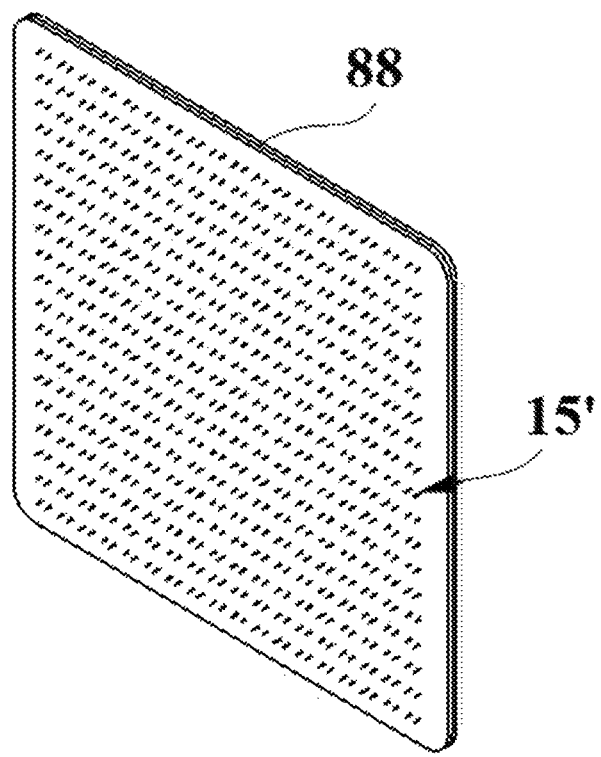
Figure 17E:
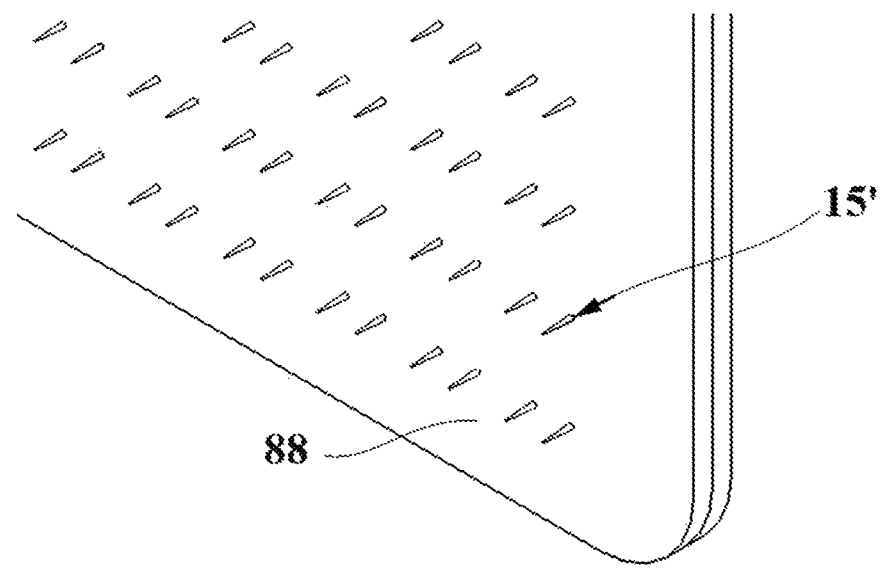

Individual tissue capture element embodiments (for example the tissue capture element depicted in FIG. 2D) could possibly tear out of the flexible base material after deployment into the target tissue if a suitable removal force is applied to the flexible base material/tissue capture element assembly. To that end, a supportive mesh 82 is shown in FIG. 17A. The supportive mesh 82 incorporates holes 84 in order to confine the tissue capture elements. The supportive mesh can consist of a fabric or metallic weave, or can simply be a sheet of flexible yet resilient material with a pattern of holes cut into it. FIG. 17B depicts the supportive mesh 82 with tissue capture elements in their deployment state 15' placed into the mesh such that the tissue capture elements are aligned with the holes/gaps in the mesh. FIG. 17C is an exploded view showing flexible base material 19 being molded over the supportive mesh 82 and the tissue capture elements in their deployment state 15'. FIG. 17D shows the complete assembly 88 comprised of the supportive mesh 82, the tissue capture elements 15', and the flexible base material 19. Although FIG. 17C shows an exploded view, the overmolding is a continuous process. FIG. 17E depicts a close up view of FIG. 17D showing the tissue capture elements in their deployment state 15' and the supportive mesh/flexible base material assembly 88. The scale of the tissue capture elements is greatly exaggerated in FIGS. 17B-17E in order that they can be clearly seen in each figure.

Figure 18A:
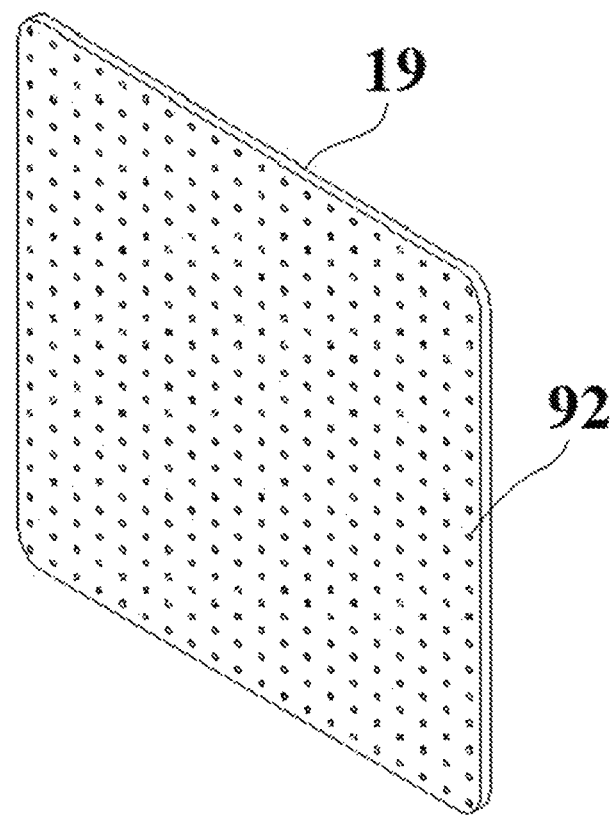
FIGS. 18A-D depict the formation of a tissue capture element/flexible base material assembly with holes to allow for the passage of gases and fluids through the flexible base material.
Figure 18B:
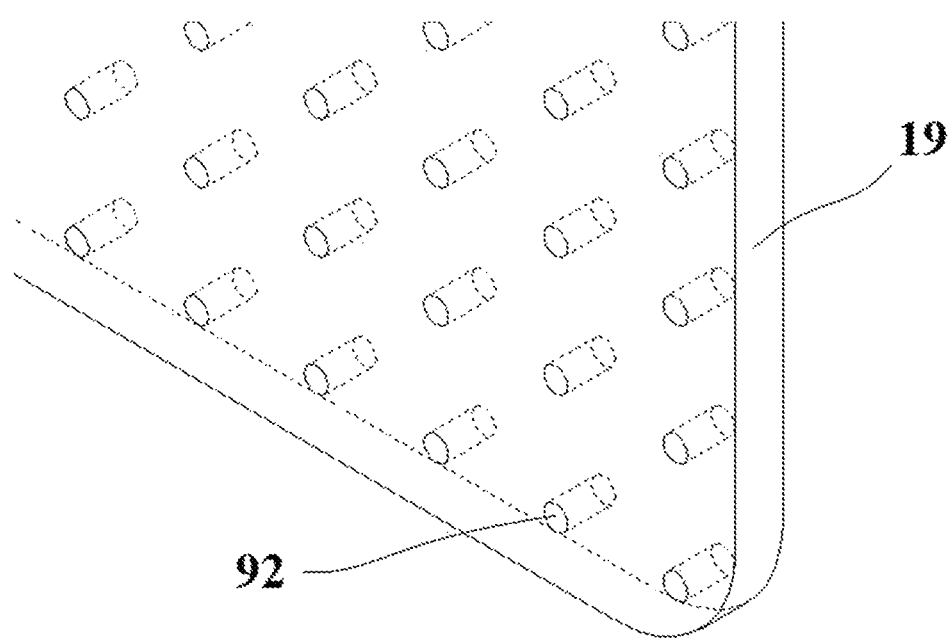
Figure 18C:
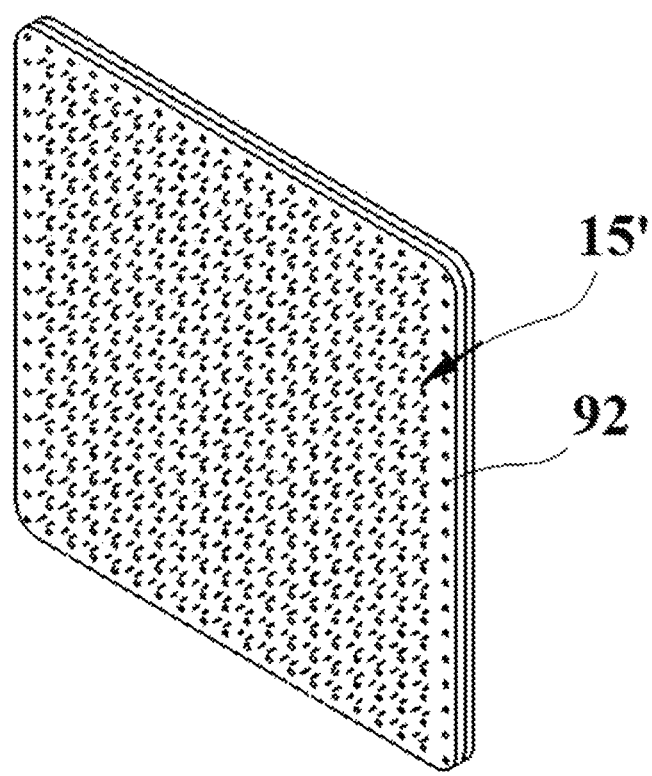
Figure 18D:
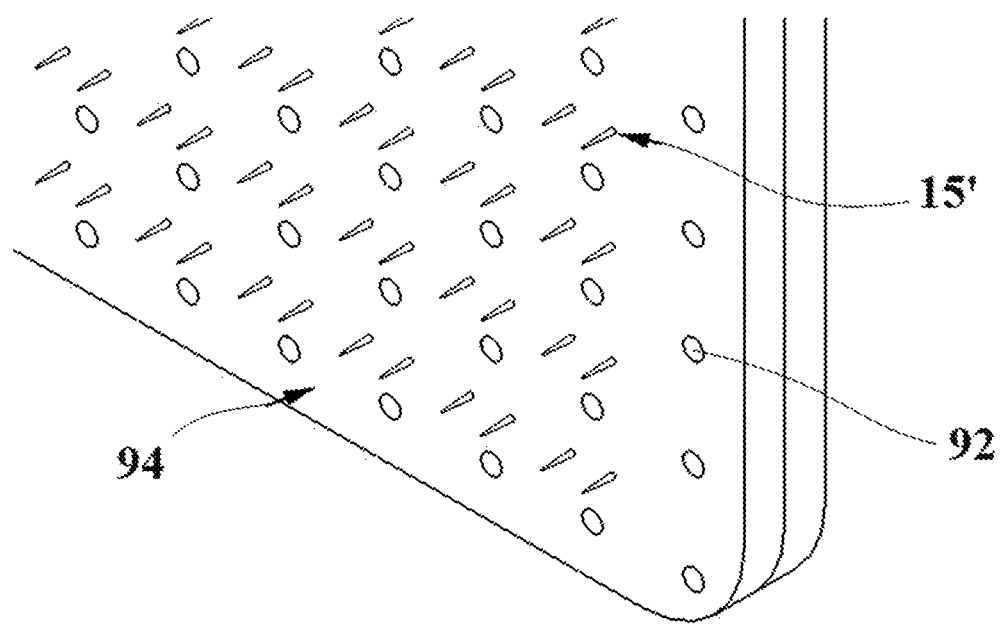

The addition of drainage holes to the flexible base material would allow for the passage of fluids and gases from the target wound to the surface outside of the flexible base material. FIG. 18A shows a section of flexible base material 19 with holes 92 formed into it creating a porous pad. FIG. 18B is a close up view of the section showing the flexible base material pad 19 and the drainage holes 92. Although the drainage holes 92 are depicted as thru holes in the figure, the flexible base material could be fabricated such that it is extremely porous thus allowing for the transfer of gases and fluids through the material. FIG. 18C depicts a pad assembly 90 comprised of flexible base material 19 and tissue capture elements in their deployment state 15'. The flexible base material incorporated holes 92 for the transfer of gases and fluids through the material. FIG. 18D is a close up view of FIG. 18C depicting the assembly 94, the tissue capture elements in their deployment state 15', and the drainage holes 92. The scale of the tissue capture elements is greatly exaggerated in FIGS. 18C and 18D in order that they can be clearly seen in each figure.

Figure 19A:
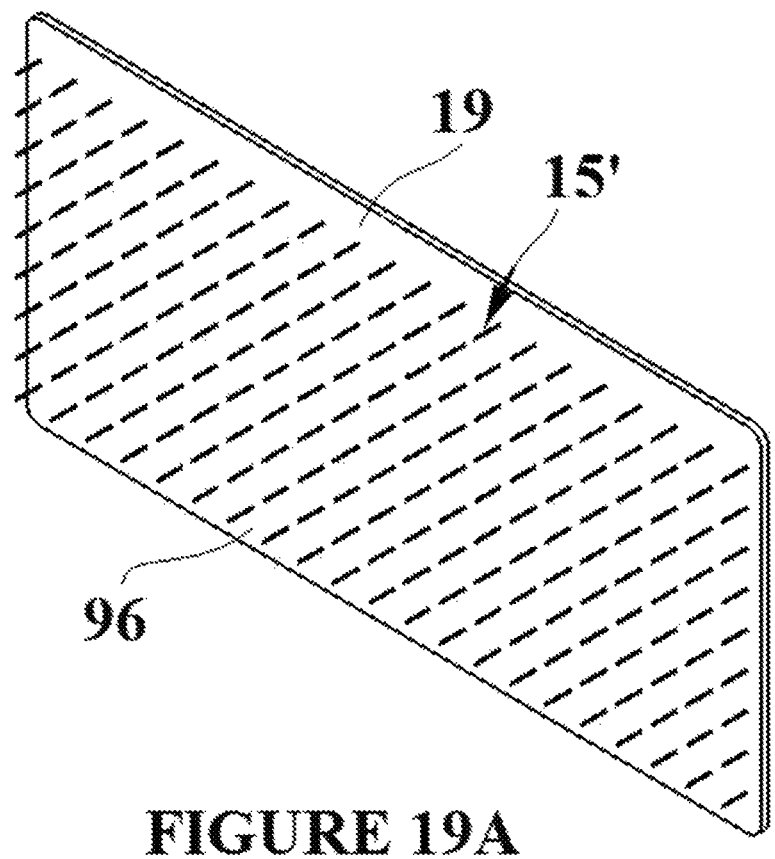
FIGS. 19A-D depict a deployment of the tissue capture element/flexible base material assembly with the flexible base material being used as a platform for bonding to itself.
Figure 19B:
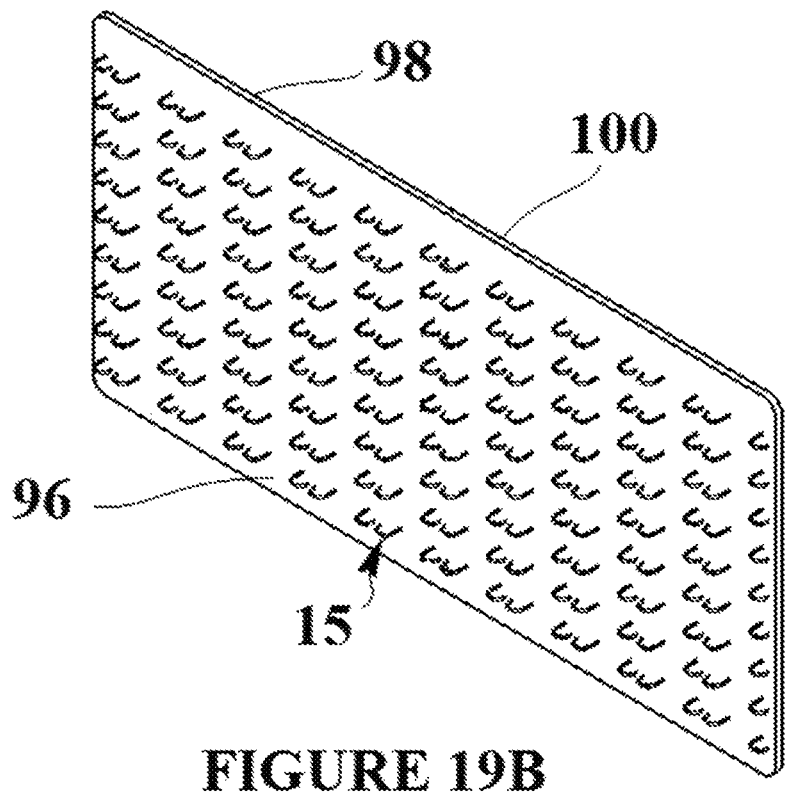
Figure 19C:
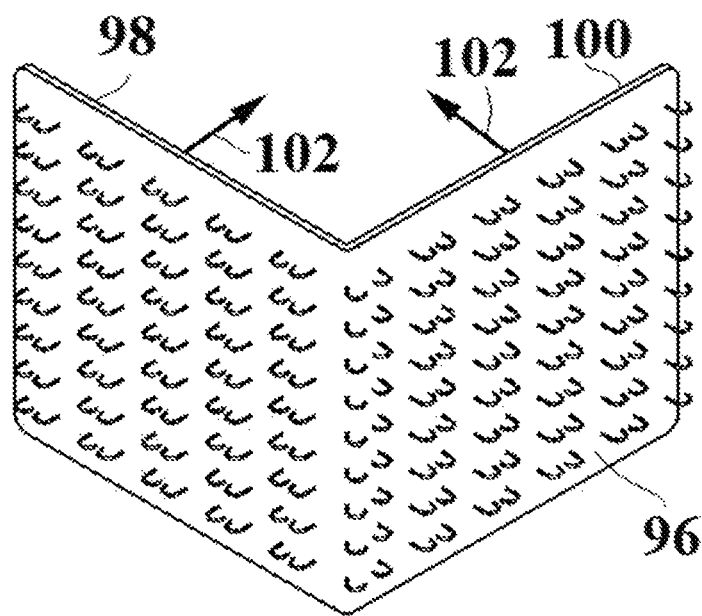
Figure 19D:
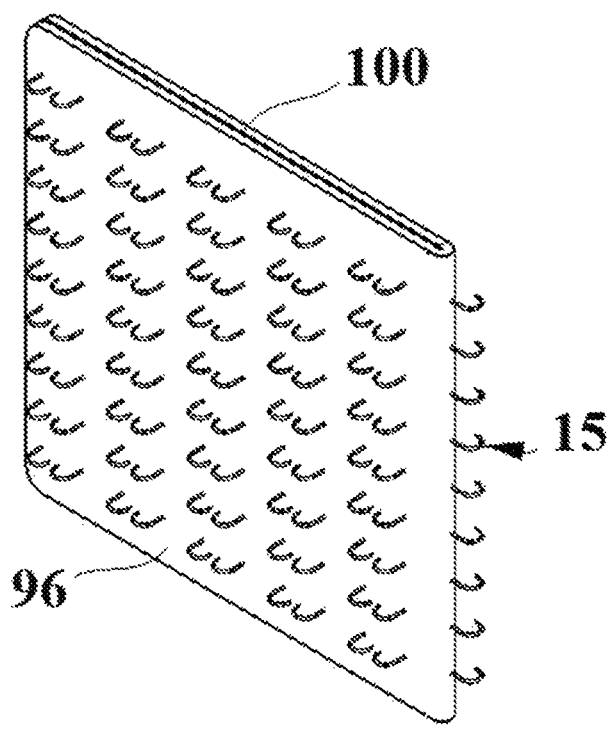

The flexible base material can act as a platform for bonding two sections of tissue together. The ability of the flexible base material to bond to itself allows for the adhesion of two sections of tissue that could otherwise not be bonded due to the presence of moisture. The flexible base material can therefore be bonded to itself in any suitable configuration in order to close a wound or reshape the target tissue. FIG. 19A shows a section of flexible base material 19 with integrated tissue capture elements in their deployment state 15'. A deployment of the section into the target tissue and subsequent bonding of the flexible bas material 19 to itself is described by the following. The tissue capture elements 15' are deployed into the target tissue such that the target tissue is flush with surface 96 of the flexible base material. FIG. 19B depicts the tissue capture elements in their engagement state 15, a process which captures the target tissue and holds it flush to surface 96. A suitable adhesive 100 is then applied to the surface 98 of the flexible base material that is opposite to the SMA elements engaging the tissue as shown in FIG. 19B. The surface and the tissue attached to the surface can then be folded 102 onto itself as shown in FIG. 19C. The two surfaces of the section that have the applied adhesive 100 are brought into contact and a bond is formed as shown in FIG. 19D. At all points during the procedure, the target tissue remains adhered to surface 96. The tissue has thus been reshaped and bonded together. The scale of the tissue capture elements is greatly exaggerated in FIGS. 19A-19D in order that they can be clearly seen in each figure.

Shape memory elements which are thermally activated may need to be thermally shielded prior to being deployed into the target tissue in order to avoid premature activation. To that end, an insulating foam or gel that encompasses the thermally activated shape memory elements can be added to the shape memory element/flexible base material assembly. In this example, the tissue capture elements described in FIGS. 15A and 15B are used. FIG. 20A shows a thermally insulating foam 106 which can surround the tissue capture elements in their deployment state 70' and which can sit flush on top of the flexible base material 19. During the deployment of the tissue capture elements 70' into the tissue, the tissue sits flush with the surface 108. FIG. 20B shows a side view of FIG. 20A. FIG. 20C shows the assembly as it is partially deployed into the target tissue which sits flush with surface 108. As the assembly is inserted into the target tissue, the insulating foam 106 compresses as shown in FIG. 20C. FIG. 20D shows a side view of FIG. 20C. FIG. 20E shows the assembly fully deployed into the target tissue which sits flush with surface 108. The insulating foam 106 is fully compressed. The tissue capture elements are activated into their permanent engagement state 70. FIG. 20F is a side view of FIG. 20E. It can thus be seen that the insulating foam 106 provides a thermal barrier to the region outside of the tissue during the deployment of the assembly. Again, the tissue capture are shown out of scale in order to be visible in FIGS. 20A-20F.

Figure 21A:
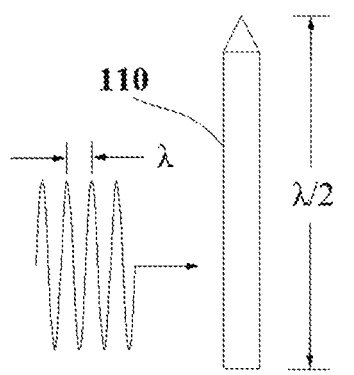

Metallic objects can act as half-wavelength antennas if the electro magnetic (EM) energy applied to them is such that the wavelength of the applied EM energy is 2 times the length of the object. Thus to "tune" the EM energy to the "antenna", the length of the object should be one half of the wavelength of the applied EM energy. The object will therefore absorb the EM energy and will heat up. This process can be applied to the thermally activated shape memory alloy element 110 in its deployment state shown in FIG. 21A. The wavelength of the applied EM energy 112 is represented by the symbol $\lambda$. The wave in the figure is not shown to scale. To calculate the frequency of the applied EM energy 112 such that it is tuned to the tissue capture element 110, the following formula is used:

$$f = \frac{c}{n*2*l}$$

Where f is the frequency of the applied EM energy, c is the speed of light ($2.9979*10^8$ m/s), n is the index of refraction of air (1.0003), and l is the length of the object. Thus for a tissue capture element of length 1 mm (0.001 m):

$$f = \frac{2.9979*10^8 \text{ m/s}}{1.0003*2*0.0001 \text{ m}} = 1.5*10^{11} hz$$

Figure 21B:
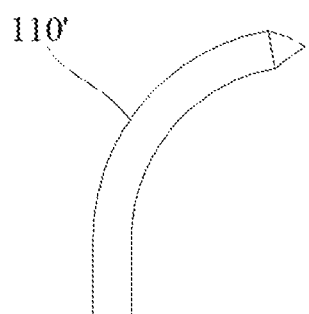

This frequency of EM energy is thus "tuned" to the 1 mm tissue capture element. The frequency is in the microwave region of the electro magnetic spectrum. When this frequency is applied to the element 110, it will heat to a temperature above its transition temperature and will transform into its engagement state 110' as shown in FIG. 21B.

Methods for the creation of elements and flexible base material and configurations thereof which comprise embodiments of the pad assemblies detailed in this document can also be used to create element and flexible base material configurations described in PCT application serial no. PCT/US09/57348 entitled APPARATUS AND METHOD FOR TISSUE ADHESION which has been incorporated by reference. These non-pad configurations may include circular and cylindrical balloon configurations, cylindrical tube configurations, and coating configurations applicable to implantable devices such as coronary stents.

Applications for embodiments contained herein and incorporated by reference can include wound care and or closure in the form of the treatment of low circulation skin ulcers such as diabetic ulcers. Other applications for embodiments contained herein and incorporated by reference include dental surgery, cardiac surgery, and battlefield dressings.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A method for employing Shape Memory Alloy (SMA) tissue capture elements comprising the steps of:
   providing a "D" shaped mandrel;
   coiling a SMA material around the mandrel;
   cutting the coiled SMA material along cut lines at a crown of the coil and proximate a radial point of the "D" farthest from a base creating opposing curved elements;
   mechanically straightening the curved elements as arms in a deployment state while the SMA material is maintained at a temperature below the transition temperature; and,
   molding an array of mechanically straightened SMA elements into a flexible tissue adhesion substrate.

2. The method of claim 1 wherein the SMA material has a transition temperature approximating a target tissue temperature and further comprising:
   inserting the arms of the SMA material into target tissue; and,
   allowing the arms to stabilize at the tissue temperature causing the arms to transform to an engagement state.

3. The method of claim 2 wherein the SMA material has a two-way shape memory further comprising:
   cooling of the target tissue surrounding the arms of the SMA material to below transition temperature; and,
   withdrawing the SMA material arms from the target tissue.

4. The method of claim 1 wherein the step of mechanically straightening includes adding beveled tips to the arms.

5. The method of claim 1 wherein the step of mechanically straightening includes mechanically flattening the base to create a flange.

6. The method of claim 1 wherein the flexible tissue adhesion substrate is configured as a tissue capture pad.

7. The method of claim 6 wherein the array of mechanically straightened SMA elements is arranged in a cross hatched pattern.

8. The method of claim 6 further comprising forming a composite two sided pad by joining a first tissue capture pad with a second tissue capture pad, the composite two sided pad having a surface one including an array of mechanically straightened SMA elements extending from the surface one, and the composite two sided pad having a surface two including an array of mechanically straightened SMA elements extending from the surface two.

* * * * *